(12) United States Patent
Hoon et al.

(10) Patent No.: US 7,897,336 B2
(45) Date of Patent: Mar. 1, 2011

(54) MOLECULAR LYMPHATIC MAPPING OF SENTINEL LYMPH NODES

(75) Inventors: Dave S. B. Hoon, Los Angeles, CA (US); Bret Taback, Santa Monica, CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 1064 days.

(21) Appl. No.: 10/641,595

(22) Filed: Aug. 15, 2003

(65) Prior Publication Data
US 2005/0142556 A1   Jun. 30, 2005

Related U.S. Application Data

(60) Provisional application No. 60/403,872, filed on Aug. 16, 2002.

(51) Int. Cl.
*C12P 19/34* (2006.01)
*C07H 21/04* (2006.01)

(52) U.S. Cl. .................. 435/6; 435/91.1; 435/91.2; 536/23.5; 536/24.33; 536/25.3

(58) Field of Classification Search ............... 435/6, 435/91.1, 91.2; 536/23.5, 24.31, 24.33, 25.3
See application file for complete search history.

(56) References Cited

U.S. PATENT DOCUMENTS

| | | | | |
|---|---|---|---|---|
| 5,451,505 | A * | 9/1995 | Dollinger ................. | 435/6 |
| 6,057,105 | A | 5/2000 | Hoon et al. ................ | 435/6 |
| 6,583,336 | B1 | 6/2003 | Reiss et al. ............... | 800/278 |
| 6,632,934 | B1 * | 10/2003 | Moreadith et al. ......... | 536/23.1 |
| 6,673,621 | B1 * | 1/2004 | Mitchell ................... | 436/56 |
| 2002/0123845 | A1 * | 9/2002 | Henning et al. ........... | 702/19 |
| 2003/0077624 | A1 * | 4/2003 | Yang et al. ................ | 435/6 |
| 2003/0157486 | A1 * | 8/2003 | Graff et al. ............... | 435/6 |
| 2004/0110290 | A1 * | 6/2004 | June et al. ................. | 435/372 |

OTHER PUBLICATIONS

Wisner et al. J. Med. Chem. 1997, vol. 40, p. 3992-3996.*
Garcia-Olmo et al. Cancer Letters, 1999, vol. 140, p. 11-20.*
Bilchik et al., "Universal application of intraoperative lymphatic mapping and sentinel lymphadenectomy in solid neoplasms," *J. Cancer*, 4(6):351-358, 1998.
Bilchik et al., "Molecular staging of early colon cancer on the basis of sentinel node analysis: a multicenter phase II trial," *J. Clin. Oncol.*, 19(4):1128-1136, 2001.
Bostick et al., "Detection of metastases in sentinel lympph nodes of breast cancer patients by multiple-marker RT-PCR," *Int. J. Cancer*, 79:645-651, 1998.
Bostick et al., "Letter to the editor," *N. Engl. J. Med.*, 339(22):1643-1644, 1998.
Bostick et al., "Comparison of blue dye and probe-assisted intraoperative lymphatic mapping in melanoma to identify sentinel nodes in 100 lymphatic basins," *Arch. Surg.*, 134:43-49, 1999.

Bostick et al., "Prognostic significance of occult metastases detected by sentinel lymphadenectomy and reverse transcriptase-polymerase chain reaction in early-stage melanoma patients," *J. Clin. Oncol.*, 17:3238-3244, 1999.
Cochran et al., "The Augsberg consensus: techniques of lymphatic mapping, sentinel lymphadenectomy, and completion lymphadenectomy in cutaneous malignancies," *Cancer*, 89:236-241, 2000.
Cox et al., "Guidelines for sentinel node biopsy and lymphatic mapping of patients with breast cancer," *Ann. Surg.*, 227(5):645-653, 1998.
Disbrey and Rack, *Histological Laboratory Methods*, (ed.) E. & S. Livingstone, 1970.
Giuliano et al., "Lymphatic mapping and sentinel lymphadenectomy for breast cancer," *Ann. Surg.*, 220(3):391-401, 1994.
Giuliano et al., "Improved axillary staging of breast cancer with sentinel lymphadenectomy," *Ann. Surg.*, 222(3):394-401, 1995.
Giuliano et al., "Sentinel lymphadenectomy in breast cancer," *J. Clin. Oncol.*, 15(6):2345-2350, 1997.
Giuliano et al., "Prospective observational study of sentinel lymphadenectomy without further axillary dissection in patients with sentinel node-negative breast cancer," *J. Clin. Oncol.*, 18:2553-2559, 2000.
Haigh et al., "Carbon dye histologically confirms the identity of sentinel lymph nodes in cutaneous melanoma," *Cancer*, 92(3):535-541, 2001.
Hill et al., "Lessons learned from 500 cases of lymphatic mapping for breast cancer," *Ann. Surg.*, 229(4):528-535, 1999.
Hoon et al., "Detection of metastatic breast cancer by β-hCG polymerase chain reaction," *Int. J. Cancer*, 69:369-374, 1996.
Imaginis online, "Breast Cancer Treatment," printed Jul. 2002.
Kaneda and Hoon, "DNA vaccines for cancer treatment," In:*Drugs*, 4(3):301-311, 2001.
Kelemen et al., "Sentinel lymphadenectomy in thyroid malignant neoplasms," *Arch. Surg.*, 133:288-292, 1998.
Kitagawa et al., "The role of the sentinel lymph node in gastrointestinal cancer," *Surg. Oncol. Clinics North Amer.*, 80(6):1799-1809, 2000.
Kuo et al., "Prediction of disease outcome in melanoma patients by molecular analysis of paraffin-embedded sentinel lymph nodes," *J. Clin. Oncol.*, 21(19):3566-3572, 2003.

(Continued)

*Primary Examiner*—Teresa Strzelecka
*Assistant Examiner*—Joyce Tung
(74) *Attorney, Agent, or Firm*—Fulbright & Jaworski LLP

(57) ABSTRACT

The present invention describes a method for identification and labeling of sentinel lymph nodes (SLNs) and the presence or absence of lymph node metastases as an important diagnostic and prognostic factor in early stage cancers of all types. The method, know as Molecular Lymphatic Mapping, uses traditional dye/radioactive tracer based techniques in conjunction with a nucleic acid marker to identify and label the SLN, not only for current diagnostic methods, but for archival purposes. In addition, MLM can be used to deliver a therapeutic gene or genes to the SLN to activate tumor immunity to tumor cells, and/or to inhibit tumor metastases. The methods may be combined with therapeutic intervention including chemotherapy and radiotherapy.

52 Claims, 11 Drawing Sheets

OTHER PUBLICATIONS

Liptay et al., "Intraoperative sentinel lymph node mapping in non-small-cell lung cancer improves detection of micrometastases," *J. Clin. Oncol.*, 20(8):1984, 2000.

Morton et al., "Technical details of intraoperative lymphatic mapping for early stage melanoma," *Arch. Surg.*, 127:392-399, 1992.

Morton et al., "Validation of the accuracy of intraoperative lymphatic mapping and sentinel lymphadenectomy for early-stage melanoma," *Ann. Surg.*, 230(4):453-463, 1999.

Saha et al., "Technical details of sentinel lymph node mapping in colorectal cancer and its impact on staging," *Ann. Surg. Oncol.*, 7:120-124, 2000.

Shoab et al., "A suggested method for sentinel node biopsy in SCC of the head and neck," *Head Neck*, 22:733-735, 2000, Technetium[99].

Tsioulias et al., "Lymphatic mapping and focused analysis of sentinel lymph nodes upstage gastrointestinal neoplasms," *Arch. Surg.*, 135:926-932, 2000.

Turner et al., "Histopathologic validation of the sentinel lymph node hypothosis for breast carcinoma," *Ann. Surg.*, 226:271-276, 1997.

Uren et al., "Lymphoscintigraphy in high-risk melanoma of the trunk: predicting draining node groups, defining lymphatic channels and locating the sentinel node," *J. Nucl. Med.*, 34(9):1435-1440, 1993.

Veronesi et al., "Sentinel-node biopsy to avoid axillary dissection in breast cancer with clinically negative lymph-nodes," *Lancet*, 349:1864-1867, 1997.

Wascher et al., "Detection of MAGE-A3 in breast cancer patients' sentinel lymph nodes," *Br. J. Cancer*, 85(9):1340-1346. 2001.

Wawroschek et al., "Radiosotope guided pelvic lymph node dissection for prostate cancer," *J. Urol.*, 166(5):1715-1719, 2001.

Bieligk et al., "Detection of tyrosinase mRNA by reverse transcription-polymerase chain reaction in melanoma sentinel modes," *Annals of Surgical Oncology*, 6(3):232-240, 1999.

Ghossein et al., "Molecular detection of micrometastases and circulating tumor cells in solid tumors," *Clinical Cancer Research, American Assoc. for Cancer Research*, 5(8):1950-1960, 1999.

Noguchi et al., "Detection of breast cancer micrometastases in axillary lymph nodes by means of reverse transcriptase-polymerase chain reaction," *American J. of Pathology*, 148(2):649-656, 1996.

Taback et al., "Molecular lymphatic mapping of the sentinel lymph node," *American Journal of Pathology*, 161(4):1153-1161, 2002.

\* cited by examiner

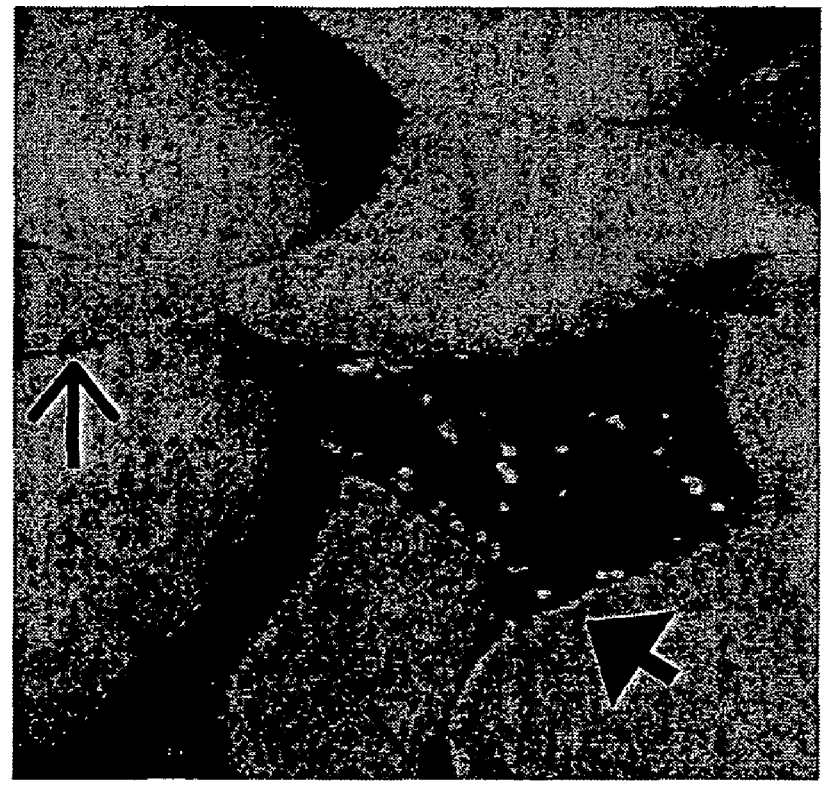
FIG. 2A-B

MOLECULAR LYMPHATIC MAPPING OF SENTINEL LYMPH NODES

The present application claims benefit of priority to U.S. Provisional Ser. No. 60/403,872, filed on Aug. 16, 2002, the entire contents of which are hereby incorporated by reference.

BACKGROUND OF THE INVENTION

1. Field of the Invention

The present invention relates generally to the fields of surgery, cancer and histopathology. More particularly, it concerns a method for identification and labeling of sentinel lymph nodes as part of the prognostic and diagnostic evaluation of cancer. In particular aspects, the present invention relates to use of a molecular markers, optionally in conjunction with dyes/tracers, to identify and label sentinel lymph nodes in cancers such as breast cancer, gastrointestinal cancers and melanoma.

2. Description of Related Art

The technique of intraoperative lymphatic mapping and sentinel lymph node (SLN) dissection has revolutionized the management of regional tumor-draining lymph nodes in melanoma and other solid cancers that metastasize via the lymphatics. The procedure is minimally invasive and reduces morbidity. Furthermore, this approach provides for a more focused assessment of occult metastasis in a cost-effective manner, which may improve clinicopathological staging. Since Morton et al. (1992) introduced the technique in melanoma, it has been successfully applied to breast cancer (Giuliano et al., 1994; Giuliano et al., 1995), colon cancer (Saha et al., 2000; Bilchik et al., 1998), thyroid cancer (Kelemen et al., 1998), gastric cancer (Kitagawa et al., 2000), head & neck cancer (Shoaib et al., 1999), lung cancer (Liptay et al., 2002) and prostate cancer (Wawroschek et al., 2001).

Because the SLN is the first lymph node to harbor metastatic cancer cells from the primary tumor, its tumor status is highly predictive of the histopathology of the associated lymphatic drainage basin. It has been shown that patients who have tumor-free SLN do not need a complete lymph node dissection, thus avoiding the cost and potential morbidity associated with a formal elective lymph node dissection (Morton et al., 1992; Kitagawa et al., 2000; Tsioulias et al., 2000; Giuliano et al., 1997; Brobeil et al., 1999). The clinical benefits of SLN dissection are currently being assessed in several large ongoing multicenter randomized trials for melanoma, breast and colon cancer (Veronesi et al., 1997; Giuliano et al., 2000; Morton et al., 1999; Haigh and Giuliano, 2000; Harlow and Krag, 2001; Bilchik et al., 2001).

Concurrent with the development of the SLN procedure in the 1990's, the inventors' laboratory has been developing molecular detection approaches to improve identification of occult metastatic tumor cells in the SLN(s) of melanoma, breast cancer, and colon cancer patients (Bilchik et al., 2001; Hoon et al., 1996; Bostick et al., 1998a; Bostick et al., 1998b; Bostick et al., 1999b; Wascher et al., 2001). The inventors have shown in frozen sections of SLN, using multimarker RT-PCR assays, that melanoma, colon and breast cancer patients can be upstaged compared to H&E and IHC analysis (Bilchik et al., 2001; Bostick et al., 1998a; Bostick et al., 1999b). More recently, through extensive studies, it has become known that IHC detection for micrometastasis and occult tumor cells in the SLN is more efficient if carried out on paraffin-embedded sections compared to frozen sections. This approach also minimizes the variability of analysis among institutes. Studies in the inventors' laboratory have evolved to assess for metastatic tumor cells in paraffin-embedded SLN.

Although the SLN is highly predictive of the histologic status of the tumor-draining lymph node basin when using the technique of blue dye and/or radioisotopes for detection, the ability of these reagents to accurately categorize draining lymph node hierarchy is limited. This is particularly true when multiple lymph nodes may stain blue and/or demonstrate radioactivity. Additionally, because these substances dissolve and decay respectively over time, they lack utility as an enduring label of the sentinel node, as well as additional lymph nodes for subsequent analysis of paraffin-embedded tissues. Introduction of a durable substrate marker during surgical lymphatic mapping, which can be readily quantitated among the tumor-draining lymph nodes, would provide a unique method to accurately label the sentinel and secondary lymph nodes during the entire course of their evaluation.

SUMMARY OF THE INVENTION

Thus, in accordance with the present invention, there is provided a method for identifying sentinel lymph nodes comprising (a) administering a composition comprising a marker nucleic acid segment to a human subject regional to a sentinel lymph node; and (b) determining the presence or absence of the marker nucleic acid segment in a lymph node, wherein the presence of said marker nucleic acid segment in the lymph node identifies the lymph node as a sentinel lymph node. The marker nucleic acid segment may be a prokaryotic nucleic acid segment, such as a bacterial or viral nucleic acid segment, or a eukaryotic nucleic acid segment, such as a plant kingdom (e.g., rice) nucleic acid segment. The human subject may be at risk of cancer, including cancer metastasis. The human subject may have been diagnosed with a solid cancer, which may be believed to be in remission.

The cancer may be a solid tumor cancer such as breast cancer, gastrointestinal cancer, melanoma, squamous carcinoma, merkel cell cancer, colorectal cancer, pancreatic cancer, gastric cancer, thyroid cancer, renal cancer, bladder cancer, prostate cancer, esophageal cancer, vulvar cancer, ovarian cancer, penile cancer, lymphoma, head & neck cancer and lung cancer. The marker nucleic acid may be administered by injection into the lymphatic system proximal to the tumor-draining lymphatic basin or adjacent to or into to the solid tumor. The marker nucleic acid segment may comprise a linear, double-stranded DNA molecule or plasmid vector. The composition may further comprise a dye, such as isosulfan blue, direct sky blue, pentamine, guajazulen blue, or methylene blue. The composition may further comprise a radioactive isotope, such as technetium$^{99}$. The composition may contain a ligand such as biotin for in situ hybridization detection.

The method may further comprise the step of removing a lymph node from said subject, wherein the removal occurs after step (a) and before step (b). The removed lymph node may be frozen, and/or embedded in preserving material, such as in paraffin. The method may further comprise performing histopathology upon the removed lymph node, such as hematoxylin staining, eosin staining, immunohistochemistry, or amplification of nucleic acid. The step of identifying may comprise nucleic acid hybridization to said marker nucleic acid segment, including nucleic acid amplification of said marker nucleic acid segment (e.g., PCR, quantitative PCR, relative-quantitative PCR, real-time PCR, in situ staining). Hybridization also may comprise hybridization of a labeled probe to nucleic acids isolated from cells of the removed lymph node. The label may be a fluorophore, a radioactive isotope, or a ligand (e.g., biotin, ECL system (Amersham)). The DNA also may be attached to a bead, particle or other substrate and delivered to the lymphatic system.

The method may further comprise providing to the human subject chemotherapy, radiotherapy, gene therapy, hormonal therapy or immunotherapy. The gene therapy may comprise targeting a sentinel lymph node with a gene therapy vector comprising a cancer therapeutic coding region operably linked to a promoter active in eukaryotic cells. The gene therapy vector may comprise a nucleic acid segment encoding a tumor suppressor, an inducer of apoptosis, a cell cycle regulator, a cytokine, a toxin, or a hormone. The promoter may be a constitutive promoter, a tissue specific promoter or an inducible promoter. The gene therapy vector may be a non-viral vector, or a viral vector, such as a herpesviral vector, an adenoviral vector, a retroviral vector, a polyoma viral vector or a poxyiral vector. The gene therapy vector may be comprised within a liposome.

The method also may further comprise surgical removal of primary tumor tissue. The removed lymph node may be a sentinel lymph node. Alternatively, multiple lymph nodes may be removed. The method may further comprise assessing (such as by immunohistochemistry, nucleic acid hybridization, PCR) the presence or absence of metastatic cells in the sentinel lymph node, and optionally making a treatment decision based upon the presence or absence of metastatic cells in the sentinel lymph node. The method may further comprise staging the cancer based upon the presence or absence of metastatic cells in the sentinel lymph node. The method may further comprise assessing the presence or absence of metastatic cells in an adjacent draining lymph node, and optionally making a treatment decision based upon the presence or absence of metastatic cells in the adjacent draining lymph node. The method may further comprise staging the cancer based upon the presence or absence of metastatic cells in the adjacent draining lymph node. The method may further comprise removing a non-sentinel lymph node based upon the presence of metastatic cells in the removed sentinel lymph node.

As used herein the specification, "a" or "an" may mean one or more. As used herein in the claim(s), when used in conjunction with the word "comprising," the words "a" or "an" may mean one or more than one.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The file of this patent contains at least one drawing executed in color. Copies of this patent with color drawing(s) will be provided by the Patent and Trademark Office upon request and payment of the necessary fee. Color drawings will be included in the drawings incorporated herein as they are histological photographs.

FIGS. 2A and 2B—Representative MLM and SLN identification. Photograph shows when blue dye injected into the rat footpad (yellow arrow) as traced to the first draining popliteal lymph node (SLN) (blue arrow). FIG. 2B shows blue dye injected in the colon (yellow arrow) and traced to the first draining mesenteric lymph node (SLN) (blue arrow).

(FIG. 8A) represents control SLN after MLM with blue dye only; 200×, original magnification. (FIG. 8B) represents biotinylated rDNA detection (brown) in SLN after MLM; 100×, original magnification. (FIG. 8C) represents biotinylated rDNA detection (brown) in SLN after MLM; 200×, original magnification. Sections of SLN were hematoxylin counterstained.

DESCRIPTION OF ILLUSTRATIVE EMBODIMENTS

Figure 1:
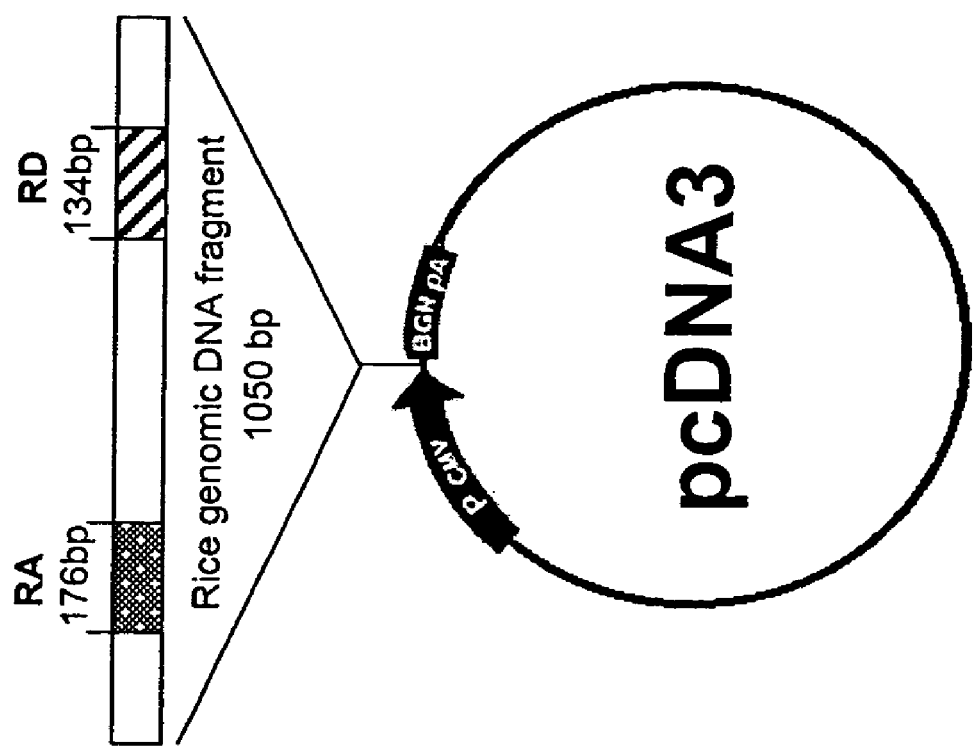
FIG. 1—Rice DNA plasmid construct. The rice DNA fragment of 1050 bp was inserted into plasmid pcDNA3. PCR amplification using RA (176 bp product) and RD (134 bp product) primers were used to detect the rice DNA fragment.

The involvement of the lymph system in solid tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is involved with the blood vascular system in developing the immune response of the lymphocytes and other cells. Lymph flows within the system as a consequence of a variety mechanisms of organ and tissue dynamics.

For certain cancers, metastasis occurring in consequence of lymph drainage will result in an initial location or positioning of neoplastic cells at certain lymph nodes typically deemed "sentinel lymph nodes" within a pertinent regional lymph drainage basin. Some cancers, for example, melanomas, have been observed to exhibit variability in lymphatic drainage patterns emanating from different portions of the body. Other cancers, such as those encountered in the breast will evidence somewhat more predictable nodal involvement.

The single most important prognostic factor for patients with early-stage melanoma and other solid neoplasm is the tumor status of the regional nodes draining the primary tumor. Until recently, the only method to identify the regional nodal metastasis was complete lymph node dissection followed by pathologic examination of each excised node using hematoxylin and eosin (H&E) staining. However, this technique samples only a small percentage of each node and therefore underestimates the true frequency of nodal metastasis. The sentinel lymph node within the regional nodal drainage basin associated with a tumor is a critical site for identification, diagnosing, prognosing, staging and predicting the presence of nodal metastasis.

In designing forms of cancer disease management, therefore, efforts are directed to the identification of affected lymph nodes. For melanomas, it has been a more recent practice to identify the pertinent disease associated drainage basin or regional nodes along with an evaluation of the extent of lymph involvement with micrometastasis. A pre-surgical step investigative procedure undertaken in melanomas involves lymphatic mapping in the form of lymphoscintigaphy. The clinician is able to generate a two-dimensional image by injecting into the tumor site a tracer, for example, sulfur colloid labeled with technetium 99-m ($^{99m}T_c$). The path of drainage and the location of the proper drainage basin is identified by the region of radioactivity at the pertinent regional lymph nodes. Sentinel nodes then are removed and submitted for pathology evaluation. The success of intraoperative lymphatic mapping depends on accurate identification of the sentinel lymph node by the nuclear medicine practitioner, its accurate removal by the surgeon and the accurate identification of metastatic tumor cells in the sentinel node.

Here, the inventors describe a new and innovative technique called Molecular Lymphatic Mapping (MLM), which can be used in conjunction with dye and/or radiocolloid labeling of SLNs for archiving, histopathology and molecular studies. A rat model system was established to demonstrate the utility of the MLM technique. A xenogeneic DNA segment with no significant homology to known rat or human genomic sequences was used to provide a highly specific marker. The inventors successfully demonstrate the effectiveness of MLM using a plasmid containing rice DNA, as well as a linear rice DNA fragment, in both frozen and paraffin-embedded SLN. The study also demonstrated MLM in targeting the first tumor-draining lymph node in the regional lymphatic basin for therapeutic intervention. rDNA was detected in the subcapsular and paratrabecular sinus of the SLN. This compares with similar observational studies using carbon dye as a lymphatic mapping agent (Haigh et al., 2001).

Initially, rice plasmid DNA was assessed to determine if a DNA vector could be effectively delivered to the SLN. However, smaller DNA fragments with no potential of integration into the host genome will be more desirable for human studies. rDNA studies demonstrate that a smaller DNA fragment was as efficient as the plasmid for MLM. Furthermore, the design of the two primer sets for the assay provides a fail-safe should potential degradation of the DNA marker occur in the SLN. This approach also improves the assay sensitivity and enhances its accuracy for marker detection. A DNA sequence approximately 0.5 kb to 5 kb is efficient in MLM for identification and labeling the SLN.

These studies, performed on frozen SLN, were adapted to paraffin-embedded SLN using both rice plasmid DNA and rDNA. No significant loss in detection of the markers was observed in paraffin-embedded SLN as compared to frozen SLN for rice plasmid DNA. The PCR detection of low dosages of rDNA from a limited number of paraffin-embedded sections demonstrates the assay sensitivity. In addition, the assay was quantitative.

Formalin fixation and paraffin-embedding for permanent sections are the standard procedures in hospitals throughout the world for archiving lymph nodes dissected from surgical operations. Though the long-term effects of such procedures on MLM are not known, in general, DNA of paraffin-embedded tissue does not significantly degrade within 10 years. In addition, as nucleic acid based assays for tumor cell detection are developed, a molecularly labeled SLN will become very important as this allows simultaneous analysis of tumor markers and SLN verification, and provides an "inherent" molecular label assessable by molecular assays.

In human melanoma, colon cancer and breast cancer SLN studies, there can be more than one SLN identified during SLN detection (Giuliano et al., 1997; Veronesi et al., 1997; Morton et al., 1999). Also depending on the method used (blue dye or radiocolloids) and the surgeon's technical expertise, multiple potential SLN may be identified during the operation (Tsioulias et al., 2000; Veronesi et al., 1997; Cochran et al., 2000; Turner et al., 1997; Bostick et al., 1999b; Cox et al., 1998; Hill et al., 1999). This can cause difficulties for pathologists analyzing and determining the true first draining SLN. The ability to quantify an inherent marker, the SLN, will provide an additional parameter to more accurately assess lymphatic distribution and appropriately label the SLNs, as well as secondary lymph nodes for correlation. This may be especially important in characterizing complex lymphatic drainage patterns, i.e., those that may occur with colorectal cancers. Thus, another objective was to determine if the DNA marker could be quantitated in the SLN. Analysis of rDNA copies in the SLN was assessed using quantitative real-time PCR. The quantitation of the rDNA was successful and provided an accurate measure of DNA copies to delineate the SLN by MLM. The distribution level of rDNA among SLN and downstream nodes can be assessed rapidly by this approach.

Secondary lymphoid organs can be very useful sites to directly augment regional and systemic immunity through lymphatic directed vaccination. To date, most gene vaccination approaches have been administered through intramuscular, s.c., or intradermal routes (Kaneda and Hoon, 2001). Unfortunately, improved approaches are needed to activate anti-tumor specific immunity in tumor-draining lymph nodes, which may act to control local, in-transit and regional recurrence. The present studies demonstrate the feasibility of rapidly (in a matter of minutes) delivering therapeutic genes to specific draining lymph nodes (i.e., SLN) in vivo. The first tumor-draining lymph node, or SLN, is important in host defense, prevention of metastasis and further spread of disease. MLM with plasmids for specific therapeutic genes, such as antigens or cytokines, can be used to target draining lymph nodes and activate regional immunity. This may be very useful in immune activation of tumor-draining lymph nodes to specific antigens, and in the induction of anti-tumor immunity or reverse tumor-induced immune suppression.

I. NEOPLASTIC TISSUE AND LYMPH NODES

The present invention can be used for identifying SLN in association with a number of cancers. Examples include lung carcinoma, melanoma, neuroblastoma, pheochromocytoma, colon, prostate and renal carcinoma, breast carcinoma, gastrointestinal, thyroid, vulvar, ovarian, rectal, renal, bladder, penile, anal, esophageal, gastric, billiary, pancreatic, oropharyngeal cancer and other neoplasms that metastasize via the lymphatics.

Melanomas are among the most serious manifestations of skin cancer and lead to a greater number of fatalities than any other form of skin cancer. Melanomas can metastasize through the lymphatic system to regional nodes and then via the blood to secondary sites on the skin or in the liver, lungs and brain. Whereas the prognosis for superficial spreading melanomas can be quite good, there is a much poorer prognosis for nodular melanomas and thicker melanomas in which distant metastases frequently form.

Breast cancer is a major cause of death for women. Breast cancers primarily spread via the lymphatics to the draining lymph nodes. The metastatic status of nodes is critical in planning treatment as well as staging for disease outcome. Occult tumor cells in breast lymph nodes can be deadly. SLN techniques have dramatically improved stage of breast cancer patients.

An evaluation of the presence or absence of tumor micrometastasis or invasion has been a major determinant for the achievement of an effective treatment for cancer patients. Studies have determined that about 30% of patients with essentially newly-diagnosed solid tumors will exhibit clinically detectable metastasis. Of the remaining 70% of such patients who are deemed "clinically free" of metastasis, about one-half are curable by local tumor therapy alone (Sugarbaker, 1981). The remaining patients will have clinically occult (undetected) micrometastasis that ultimately become manifest.

Patient management for staging purposes for the case of cutaneous melanoma is highly predicated upon determinations of lymph involvement. A number of factors are involved in the prognosis of the disease including location, tumor thickness, level of invasion, growth patterns, and of particular importance, the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial debate exists between investigators as to whether or not elective lymph node dissection or lymphadenectomy is an appropriate therapy. Elective lymphadenectomy has the major advantage of treating a nodal metastasis at a relatively early stage in its natural history when the tumor burden is low.

For cancers such as breast cancer, the sites of lymph node involvement commonly encountered are axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics as opposed to therapy. In this regard, the combination of the presence and extent of metastasis to the axilla represents the single most important prognostic factor for the management of patients with breast cancer (DeVita et al., 1993).

The axilla is a triangular region bounded by the axillary vein superiorly, the latissimus dorsi laterally, and the serratus anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by fatty tissue and visualization of them is limited. Dissection will pose risks, such as cutting the long thoracic nerve, the thoracic-dorsal nerve, the nerve to the pectoralis major or the axillary vein. Morbidity may occur in some cases due to regional node removal and patients are known to frequently discuss a numbing of the arm region following the procedure or more frequently varying degrees of lymphadema. The SLN procedure also reduces morbidity and medical expense.

While this form of somewhat radical axillary lymph node dissection has been the conventional approach to determining nodal metastatic involvement, more recent data suggests that less radical axillary node evaluation procedures may generate equivalent information for staging and patient management, but with far less dissection and resultant trauma, as discussed below. However, this requires acurate identification of SLN.

II. IDENTIFYING SENTINEL LYMPH NODES

A. Prior Techniques

Morton et al. (1992) described a procedure designed to identify that lymph node nearest the site of a melanoma and within the pertinent lymph drainage basin. Such a node, being on the most direct drainage pathway, will present the most likely site of early metastasis and is referred to as the "sentinel lymph node." Thus, by carrying out only a limited dissection specific to this node, and performing pathologic analysis thereof, staging can be achieved without at least initial resort to more radical lymphadenectomy. With this approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively stained with blue color and readily identified. Thus, the SLN of each primary melanoma is isolated and removed. By examining the sentinel nodes, for example by frozen or permanent section using routine hematoxylin-eosin histopathological techniques, as well as immunohistochemical techniques, only those patients who have evidence of micrometastasis in the draining sentinel lymph node are subject to subsequent lymphadenectomy (Morton et al., 1992; Uren et al., 1993).

The approach of Giuliano et al. (1994) also has been undertaken to moderate the otherwise somewhat radical axillary lymph node dissection common in staging breast cancer. Through the utilization of the vital dyes in conjunction with the lymph drainage system from primary breast minor, less radical SLN-based procedures may result in adequate axillary staging and regional control. With the procedure, in general, a vital blue dye, with or without the addition of a radioactive isotope, is injected into the breast mass and surrounding breast parenchyma. Following a relatively short interval, a transverse incision is made in the axilla. Blunt dissection is performed until a lymphatic tract or duct leading to a blue stained node is identified. The lymph duct, having a blue color, provides a guide path leading to the location of the most proximal lymph node and thus the sentinel node. This SLN is excised and evaluated. While the procedure calls for considerable surgical experience and talent associated with the delicate task of following the blue duct (a ruptured dye-carrying duct can be problematic), the ability to identify a tumor-free SLN will enable the surgeon to accurately stage metastasis-free breast cancer patients without subjecting them to the risks of radical dissection. The approach may also improve histologic staging by enabling the pathologist to focus on fewer lymph nodes (Giuliano et al., 1994).

B. MLM

MLM expands on previous techniques by incorporating the use of a marker nucleic acid, optionally with a dye (colored) or tracer (radioactive), as a way of identifying the SLN. The method relies on administration of a composition comprising the nucleic acid to a human subject regional to a SLN, optionally including an additional dye or tracer, and determining the presence or absence of the marker nucleic acid in a lymph node. The marker nucleic acid may be of human or non-human origin. However, if of human origin, it should be distinct from the nucleic acid normally found in sentinel lymph nodes. For example, a modified DNA molecule can be used as a marker since the SLN cells will not have it. A mutant (e.g., K-ras) or chimeric DNA sequence (e.g., Abl/Bcr or Ews/Fli) are examples. Such DNA markers can be easily detected using PNA clamping or mutation-specific amplification-based assays or amplification of specific tags on nucleic acids. Alternatively, non-human sequences may be used, including those from prokaryotic or plant sources. Delivery of the dye/tracer and nucleic acid will follow general protocols for the methods described above.

A variation of the SLN technique are provided by Turner et al. (1997). Briefly, for SLND, 3 to 5 mL of 1% isosulfan blue vital dye (Lymphazurin, Hirsch Industries, Inc., Richmond, Va.) was injected into the breast parenchyma surrounding the primary tumor or into the wall of the biopsy cavity. After approximately 3 to 7 min, a standard transverse axillary dissection incision was made just inferior to the hair-bearing region of the axilla. Blunt dissection was performed to identify a blue-impregnated lymphatic channel. The blue lymphatic then was followed proximally and distally until the first ("sentinel") node was identified. Sometimes two, and rarely more than two, blue-stained sentinel nodes were identified along the lymphatic tract. After SLND, a completion level I and II ALND was performed; if there was gross nodal involvement of the axillary nodes, then the dissection was extended to level III. The ALND specimen was submitted as a separate specimen for histopathologic examination.

Morton et al. (1999) described a mapping technique used at the John Wayne Cancer Institute based on a technique first described in 1990 before the Society of Surgical Oncology, and first published in 1992. The procedure is performed under general or regional anesthesia with a single intradermal injection of 1 to 2 cc of vital blue dye (patent blue or isosulfan blue) around the primary tumor or excisional biopsy wound. The injection site is gently massaged for several minutes before incising the regional lymph basin. The location and orientation of the incision are based on the anatomy of the regional basin, allowing for subsequent SCLND if indicated. Skin flaps made in the lymph node basin allow visual identification of the blue-stained lymphatics from the edge of the wound to the SN(s). If an SN is not identified within 20 min, a second injection of blue dye is made. All blue-stained SNs are excised; if H&E staining or immunohistochemistry reveals metastases in these nodes, complete lymph node dissection is performed.

Preoperative cutaneous lymphoscintigraphy is required and is performed in the United States with technetium-99m ($^{99m}$Tc)-labeled albumin colloid (CIS-US, Inc. Bedford, Mass.), $^{99m}$Tc sulfur colloid (CIS-US), or $^{99m}$Tc human serum albumin (Amersham Mediphysics, Arlington Heights, Ill.); colloidal antimony sulfide is used in Australia, and human albumin nanocolloid is commonly used in European centers. Approximately 18.5 to 30 MBq (0.5 to 0.8 mCi) of radiopharmaceutical is injected at the primary site. A scintillation camera documents the drainage pattern from the primary through the dermal lymphatics to the regional lymph nodes. The skin overlying the SN is marked. Because of variation in the transit speed of various radiopharmaceuticals and the distance from the primary to the regional basin, dynamic imaging is essential to differentiate SNs from secondary non-SNs. In the study, SNs are identified by 30 min; often by 4 hr SNs and non-SNs can no longer be differentiated because of migration of the radiocolloid to nodes beyond the SN.

Based on the concept of cutaneous lymphoscintigraphy and the dynamic nature of the radiopharmaceuticals used for these studies, in 1993 the authors devised the technique of intraoperative radiolymphoscintigraphy using one of three radiopharmaceuticals, and in 1994 reported studies with $^{99m}$Tc-labeled albumin before the Society of Surgical Oncology. During the initial studies, radiopharmaceutical was injected during surgery with isosulfan blue dye at the primary site. A hand-held gamma probe was then used to determine the radioactive count over a background site, over the afferent lymph channels, over the skin site marked during preoperative lymphoscintigraphy, and over each blue-stained node before and after its excision. From these counts, a relative count ratio of blue-stained SNs and non-SNs was established. This relative count ratio allowed the development of a strategy for intraoperative use of the hand-held gamma probe to help identify SNs and to create a baseline level of radioactivity to help identify all blue-stained lymph nodes. The technique has been refined with studies and is now routinely performed with same-day cutaneous lymphoscintigraphy: 1 to 4 hr before surgery, the patient is brought to the nuclear medicine suite, where $^{99m}$Tc-labeled filtered sulfur colloid is injected at the primary site. This avoids intraoperative injection of the radiocolloid. Although a radioactive count two times or more greater than background is accepted as corroborative evidence of an SN, the blue coloration of a node remains the gold standard for SN identification. Centers initially used blue dye to identify SNs but now combine radiocolloid and dye.

Tsioulias et al. (2000) described a procedure using an endoscopic approach to lymphatic mapping. Before open laparotomy, an exploratory laparoscopy was performed to rule out intra-abdominal metastasis. The primary neoplasm was mobilized without extensive dissection of lymphatic channels or blood vessels. Lymphatic mapping was performed by injecting 0.5 to 1 mL of isosulfan blue dye (Lymphazurin; BenVenue Laboratories Inc., Bedford, Ohio) circumferentially around the neoplasm using a tuberculin syringe. An afferent lymphatic channel usually was visualized within a minute after injection of the dye. This channel was dissected to the first 1 to 3 blue-stained lymph nodes. Each of these SNs was marked with a silk suture. The lymphatic channel containing the blue dye was then followed proximally to the site of the primary neoplasm to ensure that there were no SNs hidden in the mesenteric fat. On occasion, visualization of the lymphatic(s) and SNs required minor dissection of surrounding tissues. After all SNs were marked, an en bloc resection of the neoplasm and the regional lymph nodes was performed in the standard fashion.

Each marked node (SN) was removed from the surgical specimen by the pathologist for focused examination using a protocol developed at the institute and initially validated for histopathologic analysis of axillary SNs draining primary breast cancers. In brief, each SN was measured and, depending on its size, bisected or sectioned at 2- to 3-mm intervals. Two 4 µm paraffin sections were cut at 2 levels 200 µm apart; one was stained with HE and the other with cytokeratin immunohistochemistry (IHC) using the AE-1/AE-3 cytokeratin antibody cocktail (DAKO, Carpinteria, Calif.). An IHC stain was considered positive when strongly positive cell clusters or individual cells with histologic or cytologic features of malignant cells could be identified. The remainder of the surgical specimen was then dissected and its nodes sampled for routine evaluation using HE. The T stage, neoplasm size, number of nodes, and number of positive nodes were recorded. In the case of carcinoid tumors, both sentinel and nonsentinel nodes were also evaluated with special chromogranin and serotonin stains.

Bilchik et al. (1998) described a number of different mapping technique for distinct cancers. For melanoma, the authors introduced intraoperative mapping using lymphoscintigraphy in January 1993 and subsequently compared sentinel node localization with intraoperative lymphoscintigraphy vs. blue dye in 100 lymphatic basins in 87 patients. In the operating room, cutaneous lymphoscintigraphy was performed by use of technetium-labeled human serum albumin or sulfur colloid to trace the drainage pattern from the primary melanoma through the dermal lymphatics to the regional nodes. The skin overlying the first draining (sentinel) node was marked. Lymphatic mapping was then undertaken in the operating room by use of 0.5 to 2.0 mL of 1% isosulfan blue dye (Lymphazuirn, Hirsch Industries, Richmond, Va.) injected intradermally at the site of the primary melanoma. If the primary lesion had already been excised, the dye was injected on either side of the scar. The blue dye typically reached the regional nodes within 5 to 10 min, and the sentinel node was excised. Sections of the sentinel node were evaluated by use of hematoxylin and eosin staining (H&E) and immunohistochemical (IHC) staining for antibodies to HMB45 and S100. If metastases weRe demonstrated, CLND was performed.

In Merkel cell carcinoma, six patients underwent intraoperative lymphatic mapping and SLND. Three patients had upper extremity lesions (finger, hand, and arm), and three had facial lesions (cheek and upper lip). Preoperative lymphoscintigraphy and lymphatic mapping were performed with a technique similar to that used for melanoma.

Five patients with small squamous cell tumors of the head and neck (T1) underwent intraoperative lymphatic mapping and SLND (three tongue, one face, one floor of mouth) after preoperative lymphoscintigraphy. Isosulfan blue dye (Lymphazurin, 0.5 mL) was injected into the submucosa of the tumor with a tuberculin syringe. Five minutes later, the sentinel node was removed and sent for frozen section. A complete neck dissection was performed if the sentinel node was positive.

Between July 1994 and October 1995, 107 patients with primary breast carcinoma underwent intraoperative lymphatic mapping and SLND as previously reported. Three to 5 mL of isosulfan blue dye (Lymphazurin) was injected into the breast parenchyma immediately surrounding the primary tumor. If the primary tumor had been previously excised, the wall of the biopsy cavity and surrounding tissue were injected. A separate incision was then made in the axilla; the dye-laden lymphatic tract was identified and then followed to a blue-stained sentinel node, which was excised and processed as a separate specimen. CLND was completed through the same incision. A modified radical mastectomy or a breast-conserving surgery was then performed. Sentinel nodes were bivalved, and a frozen section was obtained to confirm the presence of nodal tissue. Sentinel specimens were then processed for permanent section with H&E. Nodes that were negative by H&E were evaluated by IHC staining by use of an antibody cocktail (MAK6 Ciba Corning, Alameda, Calif.) directed against low and intermediate molecular weight cytokeratin. Nonsentinel nodes were then analyzed by H&E.

Between August 1994 and October 1996, 17 patients underwent thyroidectomy with intraoperative lymphatic mapping and SLND. Inclusion criteria were at least one thyroid nodule suspected of malignancy and no palpable evidence of cervical lymphadenopathy. Isosulfan blue dye (Lymphazuirin, 0.5 mL) was injected into the thyroid nodule with a tuberculin syringe. Within seconds, the blue dye was seen to pass through lymphatic channels toward the sentinel node. All nodes that stained blue were excised and sent for frozen section and permanent pathologic evaluation with H&E staining and cytokeratin IHC staining.

Between 1994 and 1998, 14 patients with gastrointestinal/gynecologic malignancies (three pancreas, five colon, three small bowel, and three vulva) underwent lymphatic mapping and SLND. Patients were included if they had evidence of early cancer (stage (I or II) without extension through the muscle wall. Patients underwent a diagnostic work-up consisting of blood tests, ultrasonography, colonoscopy, and computed tomographic scan of the abdomen and pelvis. At the time of surgery, 0.5 mL of isosulfan blue dye (Lymphazurin) was injected into the submucosal margins of the tumor. A lymphatic channel could be identified within 30 sec passing toward the sentinel lymph node in all cases. The sentinel node was then excised and sent for frozen section as well as permanent pathologic evaluation. In addition to routine H&E staining, serial sections were analyzed by IHC staining for cytokeratin as well as for neuroendocrine markers (if applicable). After the sentinel node was identified, a dissection was performed to include the blue node as well as the surrounding regional lymph nodes.

Giuliano et al. (2000) performed lymphatic mapping and SLND using vital dye. In the last 6 months of the study, patients with medial hemisphere lesions underwent preoperative breast lymphoscintigraphy to document lymphatic drainage to the axilla. Isosulfan blue dye (1% Lymphazurin; Hirsch Industries Ind., Richmond, Va.) was injected around the edge of the lesion, or through the localizing needle in the case of a nonpalpable lesion. If an excisional biopsy had been performed, dye was injected into the wall of the biopsy cavity at its periphery. After 3 to 7 min, depending on the distance of the tumor from the axilla, the axillary incision was made. Blue-stained afferent lymphatics were identified using blunt dissection and traced to all blue-stained sentinel nodes, which were excised and sent for frozen section. Segmental or total mastectomy was completed. Completion ALND was performed at the time of SLND if no sentinel node was identified or if a frozen section of this node contained tumor cells. ALND was performed as a second procedure after SLND if a permanent section of the sentinel node contained tumor cells revealed by hematoxylin-eosin (H&E) staining and/or immunohistochemistry (IHC). Patients whose sentinel nodes were tumor-free did not undergo ALND. Closed-suction draining of the axilla was used for all patients undergoing ALND. Axillary drainage was not used for patients undergoing SLND alone.

C. Dyes and Chromophores

Optical imaging with dyes permit visualization of biological activities (Blasdel et al., 1986; Grinvald et al., 1988; Kauer et al., 1988; Lieke et al., 1989). Dyes that are sensitive to physicochemical environments (such as pressure, cell membrane potential, ion concentration, acidity, partial pressure of oxygen, etc.), are subject to changes in absorption or emission of light. The resulting changes act as optical probes to transform biological activities into optical signals that can be converted into optical images.

Water soluble dyes are particularly well-suited, including acid dyes, basic dyes, direct dyes, and so on, and equivalents thereof. The dye composition may be prepared as a dry material for ease of storage and packaging. If prepared as a dry composition, prior to usage the composition may be prepared as a solution using a suitable liquid, including water and various organic solvents, or mixtures thereof and so on, by techniques well known to those skilled in the art. It is particularly preferred that compatible dyes are used, with a particularly preferred embodiment utilizing anionic dyes. Although the method of formulating may be accomplished using various amounts of dyes, a particularly preferred composition employs a total dye concentration of from about 0.1 to about 10 mM. Further, the stability of the reference materials will be increased when high purity dyes, which are either commercially available or purified, using conventional methods known to those skilled in the art, are used in formulation.

Several dyes exist that can be used for visualization of lymph nodes. These include methylene blue, Tartrazine (CI 19140), Quinoline Yellow (CI 47005), Eosin (CI 45380), Acid Phloxine (CI 45410), Erythrosine (CI 45430), Sunset Yellow FCF (CI 15985), Acid Violet 5B (CI 42640), Patent Blue AF (CI 42080), Brilliant Cyanine 6B (CI 42660), Acid Brilliant Blue FCF (CI 42090), Naphthalene Green VSC (CI 44025) and Acid Blue Black 10B (CI 20470); and direct dyes such as Paper Yellow GG (CI Direct Yellow 131), Direct Scarlet 4BS (CI 29160), Congo Red (CI 22120), Violet BB (CI 27905), Direct Sky Blue 5B (CI 24400), Pentamine, Phthalocyanine Blue (CI 74180), Black G (CI 35255) and Deep Black XA (CI Direct Black 154). The CI number in the description above indicates the identification number in the Color Index, 3rd Ed., The Society of Dyers and Colorists, Bradford, Yorkshire (1971). Prefered dyes include Isosulfan blue (Patent Blue Violet, Sulfan Dye), Direct Sky Blue, Pentamine, guajazulen blue or other dye which travels through the lymphatic system.

Chromophores include Fluorescein, Rhodamine, Acid Fuchsin; Acridine Orange; Acridine Red; Acridine Yellow; Alizarin Red; Allophycocyanin; Astrazon Brilliant; Astrazon Orange R; Astrazon Red 6B; Astrazon Yellow; Bodipy Fl; Bodipy TMR; Bodipy TR; Calcein; Calcein Blue; Calcium Green; Calcium Orange; Calcofluor White; Cascade Blue; Flazo Orange; Fluorescein Isothiocyanate (FITC); Fura-2; Fura Red; Genacryl Brilliant Red B; Genacryl Brilliant Yellow 10GF; Genacryl Pink 3G; Genacryl Yellow 5GF; Granular Blue; Lucifer Yellow CH; Lucifer Yellow VS; LysoSensor Blue DND-192, DND-167; LysoSensor Green DND-153, DND-189; LysoTracker Green; LysoTracker Yellow; LysoTracker Red; Magdala Red; Magnesium Green; Magnesium Orange; Mitotracker Green FM; Mitotracker Orange; Nile Red; Nuclear Fast Red; Nuclear Yellow; Oregon Green 488; Oregon Green 500; Oregon Green 514; Phorwite AR; Phorwite BKL; Phorwite Rev; Phorwite RPA; Pontochrome; Blue Black; Procion Yellow; Pyrozal Brilliant; Rhodamine Green; Rhodamine Red; Rhodol Green Fluorophore; Rose Bengal; Sevron Brilliant Red 2B; Sevron Brilliant Red 4G; Sevron Brilliant Red B; Sevron Orange; Sevron Yellow L; Texas Red; Thiozol Orange; True Blue; and Xylene Orange.

D. Radionucleotide Tracer

Several methodologies for methods and compositions for imaging, detecting and other lymphographic techniques are known to those of skill in the art. U.S. Pat. Nos. 5,776,095, U.S. Pat. No. 5,776,094, U.S. Pat. No. 5,776,093, U.S. Pat. No. 5,728,369, and U.S. Pat. No. 4,735,210 are examples and are herein incorporated by reference.

It has been shown in the examination of lymphatic drainage of melanoma, and now shown in the lymphatic drainage of breast cancers and other solid tumors, that lymphatic drainage patterns can be defined by the injection of a radioisotope (or other traceable marker such as blue dye) into the bed of the tumor. The isotope (or dye) is then followed, either visually, with a gamma camera imaging system, or with a Geiger counter-type of counting system. Examples of radionucleotide tracers include technetium labeled sulfer or albumin colloid, antimony chloride, or other colloidal radionucleotide that travels through the lymphatic system.

It has been further shown, if one simply removes the SLN, the determination of whether or not breast cancer has metastasized to the regional lymph nodes of the axilla can be established without excision of the remaining lymph nodes in the axilla. The surgical removal of only one or a few lymph nodes greatly reduces the complications of more radical extensive lymph node surgery including the morbidity of lymphedema.

The elements of a percutaneous SLN biopsy are as follows: The tumor site in the breast is injected with a radioisotope (such as technicium$^{99m}$ labeled sulfur colloid) which travels via the lymphatic channels to the SLN. The SLN then becomes radioactively visible, or "hot." Radionucleotide detectors are able to identify or locate the radioactive lymph node through auditory and other signals, indicating when the apparatus is adjacent to the sentinel lymph node. The detectors is further able to then characterize or "visualize" the surrounding tissue with the associated ultrasound portion of the apparatus. It is important to identify the associated structures adjacent to the lymph node, because relatively large blood vessels (arteries, veins,) and nerves traverse the axilla.

With the combination of percutaneous Geiger counter identification and percutaneous ultrasound identification, the SLN can be identified and biopsied without entering a major blood vessel or severing a major nerve.

With respect to the radiolabel of choice, the ability to use a radiation detection probe that can be placed in immediate adjacency to the lymph node means that lower level energy isotopes are preferred, especially those exhibiting photon emissions of energy levels less than about 300 kev advantageously and preferably less than about 150 kev. $^{125}$I currently is the isotope of choice, although additional low energy isotopes, as disclosed in U.S. Pat. No. 4,782,840 patent, may be used as is necessary, desirable, or convenient. Higher energy level radioisotopes (e.g., $^{131}$I) also may be used, although suitable collimation of the radiation detection probe must be employed, which may impede the instrument being facile to the surgeon and limit the areas within the body cavity which can be suitably surveyed. $^{125}$I is preferred because it produces very low energy radiation and optimizes tumor contrast. Also, laparoscopic surgery can only be completed successfully with $^{125}$I.

In addition to radioisotopes emitting gamma radiation, radioisotopes exhibiting beta radiation additionally can be used in conjunction with a probe which can detect beta radiation or positrons. The detection of beta radiation intraoperatively is disclosed, for example, in U.S. Pat. No. 5,008,546, the disclosure of which is expressly incorporated herein by reference.

E. Other Reagents

A variety of radiopharmaceuticals have been evaluated for diagnostic imaging. For example, Michelot et al. (1991), Meyniel et al. (1990) and French Patent Publication 2,642, 972 by Morean et al. have disclose $^{123}$I and $^{125}$I N-(diethylaminoethyl)$_4$-iodobenzamide (i.e., IDAB) for imaging malignant melanoma in humans. Unfortunately, the synthesis of IDAB is problematic and, more significantly, IDAB is taken up in high concentrations by non-melanoma cells in the liver and lung. Accordingly, IDAB does not have optimal specificity for melanoma cells and its uptake by non-tumor cells undermines its utility for routine screening of cancer.

U.S. Pat. No. 4,279,887 to Baldwin et al., U.S. Pat. No. 5,154,913 to De Paulis et al. and Murphy et al. (1990) disclose radioiodonated benzamide compounds for use in imaging the brain only, e.g., $^{123}$I-N-β-phenethyl-o-iodobenzamide or (S)—N→(1-ethyl-2-pyrrolidinyl)methyl-2-hydroxy-3-iodo-6-methoxybenzamide (IBZM). Paramagnetic ions and ferritin labeled particles also may be used as labeling agents, and incorporated into techniques such as PET scanning. Though these techniques currently lack the spatial resolution for detection of micro- and small macro-metastatic disease, they may be used successfully in conjunction with the present invention.

Other reagents useful for identification of cancer cells and associated metastasis include any substance which preferentially concentrates at the tumor sites by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No. 4,946,778) and like substances have been developed and may similarly prove efficacious. Biochemistry and genetic engineering may yet produce substances which mimic the function of antibodies in selectively concentrating at the sites of neoplastic tissue (perhaps, even hormones, peptides and other proteins, or the like), though such substances may not be encompassed by the traditional definition of "antibody." One may also use nucleic acids attached beads, such as biodegradable beads, particles or other substrates.

F. Nucleic Acid Detection

In accordance with the present invention, the following methods are provided for the detection of nucleic acids following administration to a patient's lymphatic system. Such methods are suitable for use in vivo, with freshly isolated tissues, as well as archived tissue that has been fixed and stored, including frozen and paraffin embedded tissues.

1. In Vivo Methods

In MLM, nucleic acids may be detected in vivo or after removal of tissues. In vivo detection will rely on labels that can be detected in the body. Of particular interest are labels, called "tracers," amenable to nuclear medicine applications. Many tracers are radionuclides, which are administered to the patient to trace a specific physiological phenomenon by means of a special detector, often a gamma camera, placed outside the body. Some 100-300 available radiopharmaceuticals, mostly organic in nature and labeled with artificial radionuclides, such as indium$^{111}$ and gallium$^{67}$, have been used to study organs and tissues without disturbing them. Radiation exposure can be further minimized through the use of more short-lived radioisotopes, such as technetium$^{99m}$, iodine$^{123}$, which decay to stable form within hours. By coupling such molecules to nucleic acid markers of the present invention, a powerful tool is created.

Detection relies upon a special detecting device, a gamma camera, which identifies the radiopharmaceutical in the body. A gamma camera detects escaping photons, creating a two-dimensional image with the help of a computer and a video display unit. These images can even depict the regional quality of a specific function in a given organ. This process is called planar imaging or static scintigraphy. These images, when received in a fast successive fashion, create a dynamic study of the radiopharmaceutical behavior, revealing such detailed functional information as the emptying of the stomach, the breathing process in the lungs, or the pumping activity of the heart. Using modern computer technology, clinical images can be acquired at multiple angles, creating a replica of the body's cross-section, a technique called computerized tomography (CT). The two most advanced forms using radionuclides are single-photon emission computed tomography (SPECT) and position emission tomography (PET).

SPECT uses a rotating gamma camera to obtain images from multiple angles of the distribution of a conventional gamma emitting radiopharmaceutical within an organ. This technique is particularly valuable because of its unique ability to locate the exact position of a physiological abnormality in the body through a series of computer-generated bidimensional slices of the organ, from which three-dimensional pictures of the organ can be reconstructed. PET, valuable in the detection and management of cancer, employs one or several rings of stationary detectors around the patient's body to detect very strong diverging gamma-rays (511 keV) produced by the interactions of positrons (emitted by a previously administered radionuclide) with the free electrons within the body. This information is then processed to create body slices similar to those obtained by SPECT. PET has the unique ability to depict regional biochemical processes within the body and can demonstrate the biochemical foundation of neurological disorders and mental diseases.

Also envisioned as useful by the present inventors is the use of Scorpion™ probes, which confer substantial benefits in terms of test kenetics, thermodynamics and overall sensitivity (Whitcombe et al., 2000).

2. Hybridization

In in vitro embodiments, the typical approach will be the use of nucleic acid hybridization to the marker nucleic acid. "Probe" nucleotide sequences may be used for their ability to selectively form duplex molecules with complementary stretches of marker DNA, or to provide primers for amplification of DNA from samples. Depending on the application envisioned, one would desire to employ varying conditions of hybridization to achieve varying degrees of selectivity of the probe or primers for the target sequence.

The use of a probe between 13 and 100 nucleotides, but in some cases up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids in combination with an appropriate means, such as a label, for determining hybridization. A wide variety of appropriate indicator means are known in the art, including fluorescent, radioactive, enzymatic or other ligands, such as avidin/biotin, which are capable of being detected. In particular embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

3. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention. Other amplification methods include "race" and "one-sided PCR" (Frohman, 1990; Ohara et al., 1989).

4. Separation and Detection of Nucleic Acids

With methods that rely on removal of tissues, there are many more options for detection. For example, one can label the marker nucleic acid prior to administration, and detect the label. Alternatively, the marker nucleic acid can be amplified and/or separated, followed by hybridization with a secondary nucleic acid (a primer or a probe).

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

Capillary electrophoresis (CE) is now another technique suitable for nucleic acid separation. CE is an automated analytical technique that separates species by applying voltage across buffer filled capillaries. It is generally used for separating ions, which move at different speeds when the voltage is applied depending on their size and charge, but can be used for larger molecules as well. The solutes are seen as peaks as they pass through the detector and the area of each peak is proportional to their concentration, which allows quantitative determinations. Analysis includes purity determination, assays, and trace level determinations.

Analysis times are in the region of 1-30 minutes depending on the complexity of the separation. Modern instruments are relatively sophisticated and may contain fibre optical detection systems, high capacity autosamplers, and temperature control devices. Detection is usually by UV absorbance—often with a diode array. Other commercial detectors include fluorescence detection and coupling to mass spectrometers. Indirect UV detection is widely used for detecting solutes having no chromophores such as metal ions or inorganic anions. Low UV wavelengths (about 190-200 nm) are also used to detect simple compounds such as organic acids.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

5. Real Time PCR

For many applications, determining the amount of nucleic acid in a sample is just as critical as determining its presence or absence. For the sake of accuracy and precision, it is necessary to collect quantitative data at a point in which every sample is in the exponential phase of amplification (since it is only in this phase that amplification is extremely reproducible). Analysis of reactions during exponential phase at a given cycle number should theoretically provide several orders of magnitude of dynamic range. Rare targets will probably be below the limit of detection, while abundant targets will be past the exponential phase. In practice, a dynamic range of 2 to 3 logs can be quantitated during end-point relative RT-PCR. In order to extend this range, replicate reactions may be performed for a greater or lesser number of cycles, so that all of the samples can be analyzed in the exponential phase.

Real-time PCR assays are used for quantitate RT-PCR reactions, and combine the best attributes of both relative and competitive (end-point) RT-PCR. As such, they are accurate, precise, capable of high throughput, and relatively easy to perform. Real-time PCR automates the otherwise laborious process of quantitating reaction products for each sample in every cycle, with no user intervention or replicates required. Data analysis, including standard curve generation and copy number calculation, is performed automatically.

Real-Time Reporters. All real-time PCR systems rely upon the detection and quantitation of a fluorescent reporter, the signal of which increases in direct proportion to the amount of PCR product in a reaction. In the simplest and most economical format, that reporter is the double-strand DNA-specific dye SYBR® Green (Molecular Probes). SYBR® Green binds double-stranded DNA, and upon excitation emits light. Thus, as a PCR product accumulates, fluorescence increases.

The advantages of agents like SYBR® Green are that they are inexpensive, easy to use, and sensitive. The disadvantage is that SYBR® Green will bind to any double-stranded DNA in the reaction, including primer-dimers and other non-specific reaction products, which results in an overestimation of the target concentration. For single PCR product reactions with well designed primers, SYBR® Green can work extremely well, with spurious non-specific background only showing up in very late cycles.

The two most popular alternatives to SYBR® Green are TaqMan® and molecular beacons, both of which are hybridization probes relying on fluorescence resonance energy transfer (FRET) for quantitation.

TaqMan® Probes are oligonucleotides that contain a fluorescent dye, typically on the 5' base, and a quenching dye, typically located on the 3' base. When irradiated, the excited fluorescent dye transfers energy to the nearby quenching dye molecule rather than fluorescing, resulting in a nonfluorescent substrate. TaqMan® probes are designed to hybridize to an internal region of a PCR product. During PCR, when the polymerase replicates a template on which a TaqMan® probe is bound, the 5' exonuclease activity of the polymerase cleaves the probe. This separates the fluorescent and quenching dyes and FRET no longer occurs. Fluorescence increases in each cycle, proportional to the rate of probe cleavage.

Another useful reagent is "Blackhole" a quencher for Real-Time RT-PCR. It may be employed as part of a Taqman probe.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. When a molecular beacon hybridizes to a target, the fluorescent dye and quencher are separated, FRET does not occur, and the fluorescent dye emits light upon irradiation. Unlike TaqMan® probes, molecular beacons are designed to remain intact during the amplification reaction, and must rebind to target in every cycle for signal measurement.

Real-time Reporters for Multiplex PCR. TaqMan probes and molecular beacons allow multiple DNA species to be measured in the same sample (multiplex PCR), since fluorescent dyes with different emission spectra may be attached to the different probes. Multiplex PCR allows internal controls to be co-amplified and permits allele discrimination in single-tube, homogeneous assays. These hybridization probes afford a level of discrimination impossible to obtain with SYBR® Green, since they will only hybridize to true targets in a PCR and not to primer-dimers or other spurious products.

Real-time PCR requires an instrumentation platform that consists of a thermal cycler, computer, optics for fluorescence excitation and emission collection, and data acquisition and analysis software. These machines, available from several manufacturers, differ in sample capacity (some are 96-well standard format, while others process fewer samples or require specialized glass capillary tubes), method of excitation (some use lasers, while others broad spectrum light sources with tunable filters), and overall sensitivity. There are also platform-specific differences in how the software processes data.

6. Other Assays

A Peptide Nucleic Acid (PNA) is an analogue of DNA in which the backbone is a pseudopeptide rather than a sugar. PNA mimics the behaviour of DNA and binds complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

PNA oligomers are powerful probes in Southern and Northern Blotting and in applications such as FISH (Fluorescence In Situ Hybridization). Hybridization times are decreased because of the stronger binding of the PNA, and even short PNA probes bind strongly and specifically to target DNA. Short probes can be designed using extremely limited amino acid data to determine the location of coding sequences that would otherwise be impossible to isolate.

Another technique involves the use of locked nucleic acid, or LNA. LNAs have conformations that are restricted by a methylene linker that connects the 2'-O position to the 4'-C position. By convenience, all nucleic acids containing one or more LNA modifications are called LNA. LNA oligomers obey Watson-Crick base-pairing rules and hybridize to complementary oligonucleotides. LNAs provide vastly improved hybridization performance when compared to DNA and other nucleic acid derivatives in a number of situations. LNA/DNA or LNA/RNA duplexes have increased thermal stability compared with similar duplexes formed by DNA or RNA, and LNAs have the highest affinity towards complementary DNA and RNA ever reported. In general, the thermal stability of a LNA/DNA duplex is increased 3° C. to 8° C. per modified base in the oligonucleotide. The LNA modification has also been shown to increase the biological stability of nucleic acids, and fully modified LNA oligonucleotides are resistant towards most nucleases tested. These features of LNA make it highly attractive as a tool in biological research, DNA diagnostics and development of therapeutic drugs. LNA oligonucleotides can be used in applications such as capture probes, sample preparation, detection of single nucleotide polymorphisms, allele specific PCR, hybridization probes, molecular beacons, padlock probes, Taqman™ probes and probes for in-situ hybridizations, as well as antisense target validation.

G. Tissue Fixation

Fixation technique are well known to those of skill in the art. Standard fixation procedures permit long term storage of materials without sample degradation, and many techniques are compatible with decalcification, staining, microscopy, etc. Key elements include adequate liquid volumes (approx. 20 times the tissue volume). A typical fixation solutions is formalin-saline (formal-saline; formol-saline). See Disbrey & Rack (1970).

III. CANCER STAGING AND EVALUATION

The present invention is beneficial for cancer staging and evaluation. Identification of the sentinel lymph node will aid in the determination of the presence of metastatic cells in the disease associated lymph nodes. In determining how to treat a particular cancer, it also is important to stage (or grade) it, at the microscopic level, from tissue removed at the time of surgery. The purpose of examining the resected tissues in this way is to determine the extent of the local spread of the cancer, whether the margin between the resected cancerous mass and the presumably healthy tissue that is left behind is free of cancer, and/or whether there is spread of cancer cells to regional lymph nodes. The microscopic level examination of tissues removed in surgery is an index of whether or not cancer cells have spread beyond the primary cancerous mass and the cancer is likely to grow again, either locally or at distant sites.

The microscopic examination of cancerous tissue, and the tissue surrounding it that is believed normal tissue, preferably provides information as to whether there is local extension of the primary cancerous mass. This examination also provides a road map to determine which tissue in the patient may still be affected. The microscopic examination of lymph node tissue in the area around the cancerous mass, typically resected with the cancerous mass, is a factor in determining the success of the surgery and the therapy to subsequently treat the patient.

For example, in colon cancer, which is the second most common cancer in the United States and the developed world, the prognosis for survival is inversely related to the extent to which cancer cells penetrate the luminal surface of the colon into (or through) the colon wall or has spread to the regional lymph nodes. For a given depth of cancer cell penetration into the colon wall, the prognosis declines as the number of regional lymph nodes with cancer cells increases. The relationships between the local extent of cancer and post-surgery prognosis apply to most cancers, e.g., breast, prostate, melanoma, gastrointestinal, head, and neck cancer, etc. As such, the staging of cancer by microscopic level examination of lymph node tissues removed during surgery is an important part of the medical treatment of cancer patients.

Presently, the staging of cancer is performed by microscopic level examination of the removed tissue. This method does not provide sufficient accuracy to predict the likelihood that cancer has spread beyond the immediate site of the primary tumor. Thus, it does not provide assurance that all the cancer cells have been removed from the patient. Obviously, there needs to be a practical way to obtain such information.

There is only a general relationship between prognosis and the extent of the local extension of cancers; however, this relationship is not absolute. Frequently, local and/or distant (metastatic) recurrences of cancers occur in patients whose tissue sections have margins that appear free of cancer cells as do the regional lymph nodes. The inability to properly stage cancer based on examination of the removed tissue results in the cancer cure rates being quoted in terms of long-term survival, e.g., 5 or even 10 years of disease free time after surgery.

Pathologists who examine the removed tissue have no adequate means to determine whether all the cancer was in fact removed from the patient. Moreover, they do not have a method to accurately stage the tissue that they have. In attempts to derive the needed accuracy for the staging process, pathologists have developed morphologic criteria to hopefully enhance the accuracy of predicting the biologic behavior of cancers. This process was intended to distinguish between small, apparently contained cancers that will not recur and those cancers that will recur. The prediction of recurrence of the cancer is based of the morphology of the cancer cells and how they are organized.

The classification of cancer cells on the basis of their content of DNA and other biochemical measurements of cancer cells have not augmented significantly the predictive value of examining resected cancer tissues. As such, one of the problems of oncology and pathology is the well-known phenomena that some cancers behave aggressively to kill the patient while others that appear very similar, and which may be found in the same organ, behave in a relatively benign way, i.e., do not recur after the primary cancerous mass is removed.

Cancer staging has been complicated by the fact that it evolved over half a century. Many investigators agree that the most important independent pathologic factor for survival or recurrence after potentially curative surgery is the stage of cancer, which is determined by the depth of penetration into the adjoining area and the presence and number of positive lymph nodes. Other generic factors for survival have included gross appearance, lymphatic vessel invasion, blood vessel invasion, nucleolar organizer regions, character of invasive margin and tumor type, nuclear shape, lymphocytic infiltration, obstruction, perforation, and rectal bleeding, filtration, infiltrating border (lateral margins), age, grade, venous invasion, gender, obstruction, ploidy, etc.

A. Cancer Staging Systems

A number of cancer staging systems exist. In 1988, the American Joint Committee on Cancer (AJCC) and the Union Internationale Contra le Cancer (UICC) adopted a joint TNM classification scheme taking into account the number of positive nodes and also free mesothelial penetration. Yet another classification system was introduced in 1987 by Jass and colleagues. Using a Cox regression analysis, they found that the number of positive nodes, whether the invasive border was pushing or infiltrative, the presence of a conspicuous lymphocytic infiltrate, and the absence or presence of transmural penetration were independent prognostic factors. Because the Jass staging system is far more complicated than the modified Dukes and TNM systems, it has not been formally accepted by the National Surgical Adjuvant Breast and Bowel Project (NSABP) or other major clinical groups. The Gastrointestinal Tumor Study Group (GITSG) has also developed a classification system, which shares some of the features of the Jass system.

B. Molecular Approaches to Cancer Staging

Research has established that the presence or absence of disease in cells and tissues is based on whether molecules are normal in-structure and whether a normal distribution of molecules is present in a given type of cell. This has led physicians to recognize that accurate diagnoses of disease may be based on a gathering and an evaluation of information at the molecular level in cells. As such, it has now become essential to perform molecular level analysis to diagnose diseases, like cancer, at early stages for the accurate detection of specific types of disease through the examination of cells and tissues.

C. Biopsy and Evaluation of Disease-Associated Lymph Nodes

Instruments are and techniques are known for tissue sampling in combination with the present invention. For example, U.S. Pat. No. 5,111,828 to Kornberg et al. discloses a percutaneous excisional breast biopsy device having a cannula, open distal and proximal ends, and a sharp cutting surface on the distal end. A stylet extends through the cannula and includes a distal puncturing end. A localization guide wire is used to direct the instrument to a biopsy site. The cannula is moved distally to cut a desired tissue specimen, after which a descending element is pushed to the distal end of the tissue specimen, then pulled proximally to sever the specimen completely from surrounding tissue.

A significant disadvantage of the Kornberg approach is that only one tissue sample may be obtained for each insertion of the instrument into the patient's body to the biopsy site. Once the descending element has been pulled to sever the tissue sample, there is no opportunity to repeat the procedure while the instrument remains in place. Also, no means is provided to ensure that tissue to be sampled is drawn toward the distal end of the cannula 2 (or "actively captured"), thereby reducing tissue sampling efficiency.

IV. NUCLEIC ACIDS AND EXPRESSION

In accordance with the present invention, it may be desirable to express exogenous nucleic acid sequences in host cells. In particular, MLM may be used in conjunction with gene therapy targeted to the lymphatic system. The following general discussion provide information relevant to the construction and expression of nucleic acids in eukaryotic systems.

A. Vectors

The term "vector" is used to refer to a carrier nucleic acid molecule into which a nucleic acid sequence of interest can be inserted for introduction into a cell where it can be replicated. A nucleic acid sequence can be "exogenous," which means that it is foreign to the cell into which the vector is being introduced; "endogenous" means that the sequence is homologous to a sequence in the cell. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse α2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splice Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Particular embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. Coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

(i) Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

(ii) AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

(iii) Retroviral Vectors

Retroviruses have promise as gene delivery vectors in due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

(iv) Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

(v) Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

11. Liposomal Delivery

In certain embodiments, nucleic acids are delivered to the lymphatic system in conjunction with one or more lipids. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

(i) Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

(ii) Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged, i.e., anionic or cationic. Kaneda and Hoon (2001). For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

(iii) Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about –20° C. Preferably, chloroform is used as the only solvent since it is more readily evaporated than methanol.

(iv) Lipid Composition Structures

The nucleic acid associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid/nucleic acid composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL) or Superfect (Qiagen) complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

Emulsions. A lipid may be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

Micelles. A lipid may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

(v) Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In certain less preferred embodiments, phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition or a liposome, because of the instability and leakiness of the resulting liposomes.

In particular embodiments, a nucleic acid may be, for example, encapsulated in the aqueous interior of a liposome, interspersed within the lipid bilayer of a liposome, attached to a liposome via a linking molecule that is associated with both the liposome and the nucleic acid, entrapped in a liposome, complexed with a liposome, etc.

Making Liposomes. A liposome used according to the present invention can be made by different methods, as would be known to one of ordinary skill in the art. See, for example, Kaneda and Hoon (2001). Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the nucleic acid, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the nucleic acid is about 0.7 to about 1.0 μm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Mayhew et al., 1984; Cheng et al., 1987; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal nucleic acid or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1996).

Liposomes interact with cells to deliver agents via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

(vi) Liposomal Administration

The actual dosage amount of a lipid composition (e.g., a liposomal nucleic acid) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intralesionally, intraprostaticaly, intrapleurally, intratracheally, intranasally, intravitreally, intravaginally, rectally, topically, intratumorally, intramuscularly, subcutaneously, intravesicularlly, mucosally, intrapericardially, topically, locally and/or continuous infusion.

B. Vector Delivery and Cell Transformation

Suitable non-viral methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988). Through the application of techniques such as these, organelle(s), cell(s), tissue(s) or organism(s) may be stably or transiently transformed.

V. CANCER THERAPIES

In conjunction with the identification of a sentinel lymph node, the present invention provides for cancer therapy. Use of a wide variety of anti-cancer agents effective in the treatment of hyperproliferative disease are contemplated. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. This may be achieved by contacting the patient with a single composition or pharmacological formulation, or by contacting the cell with more than one distinct composition or formulation, at the same time or at distinct times—so called "combination therapies." Such combinations are particularly relevant to treatment of tumor cell resistance to chemotherapy and radiotherapy agents, sometimes referred to as multi-drug resistant cells.

A. Chemotherapy

Cancer therapies include a variety of chemical-based treatments. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Radiotherapeutic agents that cause DNA damage and have been used extensively and include what are commonly known as γ-rays, X-rays, and/or the directed delivery of radioisotopes to tumor cells. Other forms of DNA damaging radiation are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

May tumor cells bear markers that are amenable to targeting, i.e., is not present on the majority of other cells. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, gene therapy may be employed. Delivery of a vector encoding a therapeutic gene with anti-hyperproliferative effect will be utilized. A variety of proteins are encompassed within this aspect of the invention, some of which are described below.

1. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that antisense or single-chain antibody therapy directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

2. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK'S. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Mori et al., 1994; Okamoto et al., 1994; Nobori et al., 1994; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN- I, MEN-II, zacl, p73, VHL, MMAC1/PTEN, DBCCR-1, FCC, rsk-3, p27, p27/p16 fusions, p21/p27 fusions, antithrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

3. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

4. Cytokines

Another class of genes that is contemplated to be inserted into the gene therapy vectors include interleukins, inteferons, chemokines and cytokines. Interleukin 1, IL-2, IL-3, IL-4, IL-5, IL-6, IL-7, IL-8, IL-9, IL-10, IL-11, IL-12, IL-13, IL-14, IL-15, β-interferon, α-interferon, γ-interferon, angiostatin, endostatin, METH-1, METH-2, GM-CSF, G-CSF, M-CSF, lymphotactin, IP-10, and tumor necrosis factor F42K, MIP-1α, MIP-1β, MCP-1, MCP-3α, MCP-3β, RANTES, SLC, LARC, and ELC are contemplated.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6 or 7 days, or every 1, 2, 3, 4 and 5 weeks or every 1, 2, 3, 4, 5, 6, 7, 8, 9, 10, 11 or 12 months. These treatments may be of varying dosages as well.

F. Other Agents

It is contemplated that other agents may be used with the present invention. These agents include those that affect the upregulation of cell surface receptors and GAP junctions, cytostatic and differentiation agents, inhibitors of cell adehesion, or agents that increase the sensitivity of the hyperproliferative cells to apoptotic inducers. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used for anti-hyerproliferative efficacy, and can inhibitors of cell adehesion. Examples of cell adhesion inhibitors are focal adhesion kinase (FAKs) inhibitors and lovastatin.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Rice Gene Construction. Rice genomic DNA of *Olyza Sativa* encoding a cytoplasmic male sterility peptide in the mitochondria was chosen as the molecular identification marker. The rice gene library cloned in EMBL3 SP6/T7 (host strain K802) was purchased from Clonetech (Palo Alto, Calif.). A 1050 bp fragment from the rice gene genomic library was amplified by PCR primers: sense-5'CATAAG CCATCCGAAACCAGTA 3' (SEQ ID NO:1) and antisense-5' AATAGCATAGTCCAAGCGAACC 3' (SEQ ID NO:2). The PCR product was isolated by gel electrophoresis and then cloned into the pcDNA3 plasmid (InVitrogen, La Jolla, Calif.) (FIG. 1). The plasmid was subsequently transfected into *E. coli* and expanded as previously described (Okamoto et al., 1997). Large amount of plasmid was isolated and purified by QiaAmp (Qiagen Inc., Valencia, Calif.). The purified 5.6-kb plasmid DNA was used for MLM. The linear 1050 bp rice gene fragment was obtained either by digestion of the rice gene fragment cloned in the pcDNA3 plasmid with specific restriction enzymes or by PCR amplification and cDNA product isolation. The purified linear rice gene fragment will be referred to as rDNA from this point on.

Animals and Treatment. All animal studies were performed on male Sprague-Dawley or Fisher 344 rats. All studies were approved and conducted under the guidelines of the Animal Use Committee at Harbor UCLA Research and Education Institute. Rats were anesthetized with Ketamine (75 mg/kg) and Xylazine (7.5 mg/kg) mixture during MLM and SLND. MLM was performed by subcutaneously (s.c.) injecting 100 µl of 1% isosulfan blue (Lymphazurin, U.S. Surgical Corp, Norwalk, Conn.) solution mixed with different dosages of the rice DNA into the rat footpad. After approximately five min, dissection of the rat was performed. The blue stained lymph nodes (SLN) and adjacent downstream nodes were excised under the anesthetized condition. The dissected lymph nodes were frozen or formalin (10%) fixed for 48 hrs and then paraffin-embedded prior to DNA extraction.

DNA extraction and PCR analysis. DNA was extracted using DNAzol (Molecular Research Center Inc., Cincinnati, Ohio) from frozen and paraffin-embedded lymph nodes. Briefly, DNA extraction was performed on frozen lymph nodes using the DNAzol isolation protocol. The paraffin-embedded nodes were bivalved and serially sectioned into several 10 µm sections, deparaffinized with xylene, and DNA was extracted using a QIAamp kit (Qiagen Inc., Valencia, Calif.). At optimal established conditions of PCR approximately three sections were needed. For plasmid DNA analysis less number of sections were required. To evaluate the amount DNA extracted, the DNA concentration was quantitated using the Picogreen™ assay kit (Molecular Probes Inc., Eugene, Oreg.). Purified total DNA was dissolved in molecular grade water, quantified, and then PCR amplified for the rice gene. The PCR conditions were set up as previously described with 1.5 mM $MgCl_2$, 0.8 mM dNTP, 0.25 U Ampli-Taq polymerase (Applied Systems, Foster City, Calif.) (Morton et al., 1999; Hoon et al., 1996). Five sets of primers (RA, RB, RC, RD, RE) were initially designed targeting different sites within the cloned rice gene fragment and optimal PCR conditions were established for each primer set. RA (sense-CCATGTGATCGCTACTAAAG (SEQ ID NO:3), antisense-CATTGAGGAGTTTCCAGAT (SEQ ID NO:4)) and RD (sense-CCTTGTCTATGGCGGTAACT (SEQ ID NO:5), antisense-CAGGTTCAGCACGAAATC (SEQ ID NO:6)) primer sets proved most reliable following serial assessment under the following conditions: 95° C. for 10 min, followed by 40 cycles of 95° C. for 30 sec, 55° C. for 30 sec and 72° C. for 30 sec, and a final extension of 72° C. for 10 min. After PCR amplification, cDNA products were assessed by 2% agarose gel electrophoresis and ethidium bromide staining. Gel electrophoresis data were visualized and recorded using an Alphalmager (Alphalnnotech, San Leandro, Calif.). The housekeeping gene β-actin was used in all PCR assays to verify the integrity of the DNA in each sample.

Histochemistry analysis. A 962 bp segment of the rice gene was PCR amplified using a biotin labeled sense primer 5'-CCATGTGATCGCTACTAAAG-3' (SEQ ID NO:3) and unlabeled antisense primer 5'-GCT CTAGAAATAGCAT-AGTCCAAGCGAACC-3' (SEQ ID NO:7). The biotinylated rice linear DNA fragment was purified from agarose gel with QIAquick DNA purification kit (Qiagen Inc., Valencia, Calif.) and prepared for injection into the animals. To confirm the presence of rDNA, lymph nodes of rats injected with biotin labeled rice gene DNA (biotin-rDNA) were formalin fixed, paraffin-embedded, sectioned and stained. Slides of paraffin-embedded tissue sections were deparaffinized with xylene 3× for 3 min, treated with ethanol 3× for 3 min, and then hydrated with decreasing concentration of absolute ethanol. To block endogenous peroxidase activity, 0.3% hydrogen peroxide in methanol was overlaid on the sections for 20 min. To reduce non-specific binding, the sections were incubated with 20% normal human serum in PBS, pH 7.2, for 20 min. Horseradish peroxidase conjugated Neutroavidin (Pierce, Rockford, Ill.) in PBS was added to sections and incubated for 30 min. After several washes with PBS, the sections were then developed with diaminobenzidin (DAB) substrate solution (Vector Lab, Burlingame, Calif.). To remove the excess substrate, the sections were washed in deionized water for 3 min. Counter staining with hematoxylin (Mayer's Hematoxylin solution, Sigma, St. Louis, Mich.) was then performed on sections. Multiple sections from different SLN were evaluated by light microscopy and confirmed by at least two readers.

Rat tumor metastasis model. The rat MAT13672 III breast adenocarcinoma cell line (ATCC, Rockville, Md.) was cultured in RPMI 1640 medium supplemented with 10% fetal bovine serum (heat-inactivated). Cells in exponential growth phase were harvested, washed several times in RPMI 1640 medium, and prepared for injection. One million cells were injected s.c. into the footpad of syngeneic female Fisher 344 rats to establish primary tumors as previously described (Hoon et al., 1984). Approximately 14 days after injection, tumor growth (swelling) in the footpad was physically detectable. For MLM, the rDNA and 1% isosulfan blue dye mixture was injected into the primary tumor site. After approximately five min, blue dye containing SLN was dissected for assessment.

Real-Time PCR. To quantify the amount of rice gene DNA in lymph nodes of injected rats, quantitative PCR was performed using iCycler iQ Real-Time Detection System (Bio-Rad, San Diego, Calif.). Ten-fold dilutions of $10^7$ copies of the rice gene containing plasmids were PCR amplified along with DNA samples extracted from lymph nodes of injected rats. A dual labeled fluorescent resonance energy transfer (FRET) probe 5'-CCGAGGCCAGTTGAGATCAGTC-3' (SEQ ID NO:8) (Genset, LaJolla, Calif.) was designed and used in conjunction with the RGA primer sets for the PCR reaction. PCR conditions were kept the same except the addition of the dual labeled probe and the increase of $MgCl_2$ concentration from 1.5 mM to 2 mM. DNA samples were extracted from lymph nodes of rats injected with 2.5 or 1.25 µg of rDNA. DNA extracted from lymph nodes of rats injected with solution not containing rDNA was used as negative controls. Five hundred, 100, and 10 ng of DNA were used as templates for real-time PCR in the analysis of rice gene copy number. After 35 cycles of PCR, results were analyzed using iCycler iQ software. A standard curve of the threshold cycle ($C_t$) of PCR was constructed using the data collected of dilutions of rice plasmid DNA with known copy number. Sample starting rice gene copy number was determined by its threshold cycle relative to the standard curve. Negative controls were included in all experiments: reagents alone and SLN without rDNA.

Example 2

Results

Rice gene marker. In designing a marker for MLM, the following criteria are desired of the DNA marker: sufficient size to withstand degradation, ability to efficiently flow into the lymph node during MLM, and a unique sequence with no significant homology to known human or rat gene sequences. The GenBank data base search (Internet) verified that there was no significant homology between *Olyza sativa* (rice)

genomic DNA to known human or rat genes. A 1050 bp DNA fragment was selected from the mitochondrial membrane glycoprotein from exon II to V in the rice gene and cloned into pCDNA3 plasmid (FIG. 1).

The PCR primers were designed to obtain the highest efficacy in detection of the rice gene marker in frozen or paraffin-embedded tissue sections. Five different primer sets were initially developed for PCR detection of the rice DNA in the SLN after MLM. By having more than one set of primers covering different regions of the DNA, we were able to circumvent the potential problem of DNA subjected to in vivo DNase activity and also increase the detection sensitivity. The initial primer sets studied were RA, RB, RC, RD and RE which produced DNA products of 176, 198, 177, 134 and 198 bp, respectively. The primer sets covered both the 5' site and 3' site of the rice gene fragment (FIG. 1). Based on our assessment of efficacy of the primer sets and detection sensitivity when assessing rice DNA serially diluted in non-related DNA, we determined that the two primer sets, RA and RD were the most efficient.

Figure 3:
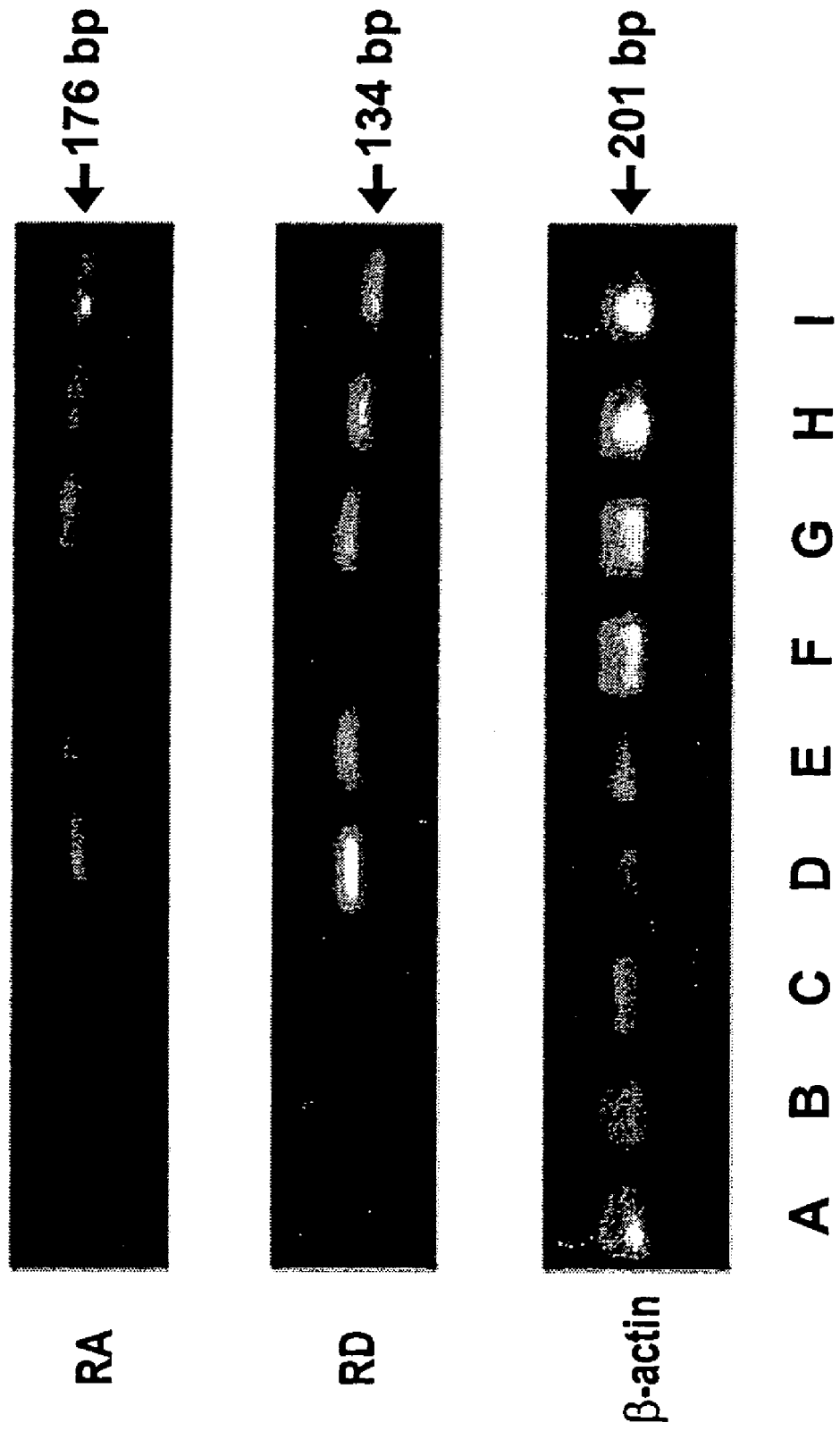
FIG. 3—Rice plasmid DNA detection by PCR in frozen SLN after MLM. Representative examples of PCR amplification with RA, RD, and β-actin on SLN. MLM performed with plasmid and blue dye in the rat footpad. Lane A is the negative control, muscle tissue. Lanes B-E are SLN (popliteal):MLM on rats was performed with 0, 0.625, 1.25, or 2.5 µg of rice plasmid DNA, respectively. Lanes F-I are mesenteric lymph nodes:MLM was performed with 0, 0.625, 1.25, or 2.5 µg of rice plasmid DNA, respectively.

MLM with plasmid DNA. In the initial MLM studies, the purified 5.6 Kb rice plasmid DNA was mixed with 1% isosulfan blue. Serial dilutions of rice plasmid DNA were assessed from 0.625 to 5 µg/100 µl. Because the 1% isosulfan blue (Lympazurin) is used for lymphatic mapping in melanoma, breast and colon cancer patients at our institute, we also used this blue dye for the animal studies. For MLM the plasmid DNA in blue dye was injected into the footpad of rats under anesthetized condition. Approximately five min after injection of the plasmid DNA and dye solution, an oblique incision was made in the popliteal fossa to identify the first draining lymph node (SLN). The blue dye stained lymph node (FIG. 2) was excised for PCR analysis. To confirm whether injected DNA had reached the popliteal node (SLN), PCR analysis was performed on the frozen SLN. The SLN was then thawed, DNA extracted, and PCR amplified with the two optimal rice gene primer sets RA and RD. Representative examples of DNA marker detection using different dosages of plasmid DNA in MLM are shown in FIG. 3. The DNA marker could be detected using three serial sections from lymph nodes when 1.25 and 2.5 µg were used for MLM. In Table 1, a summary of the detection efficacy of plasmid DNA of 2.5 µg after MLM is shown. In a representative experiment, only one of four SLN was negative for the rice DNA. However, using both primer sets RA and RD, the rice plasmid DNA was always detected in the SLN after MLM. All SLN isolated from control animals in which LM was performed with isosulfan blue only were negative for the rice DNA marker by PCR analysis.

Figure 4:
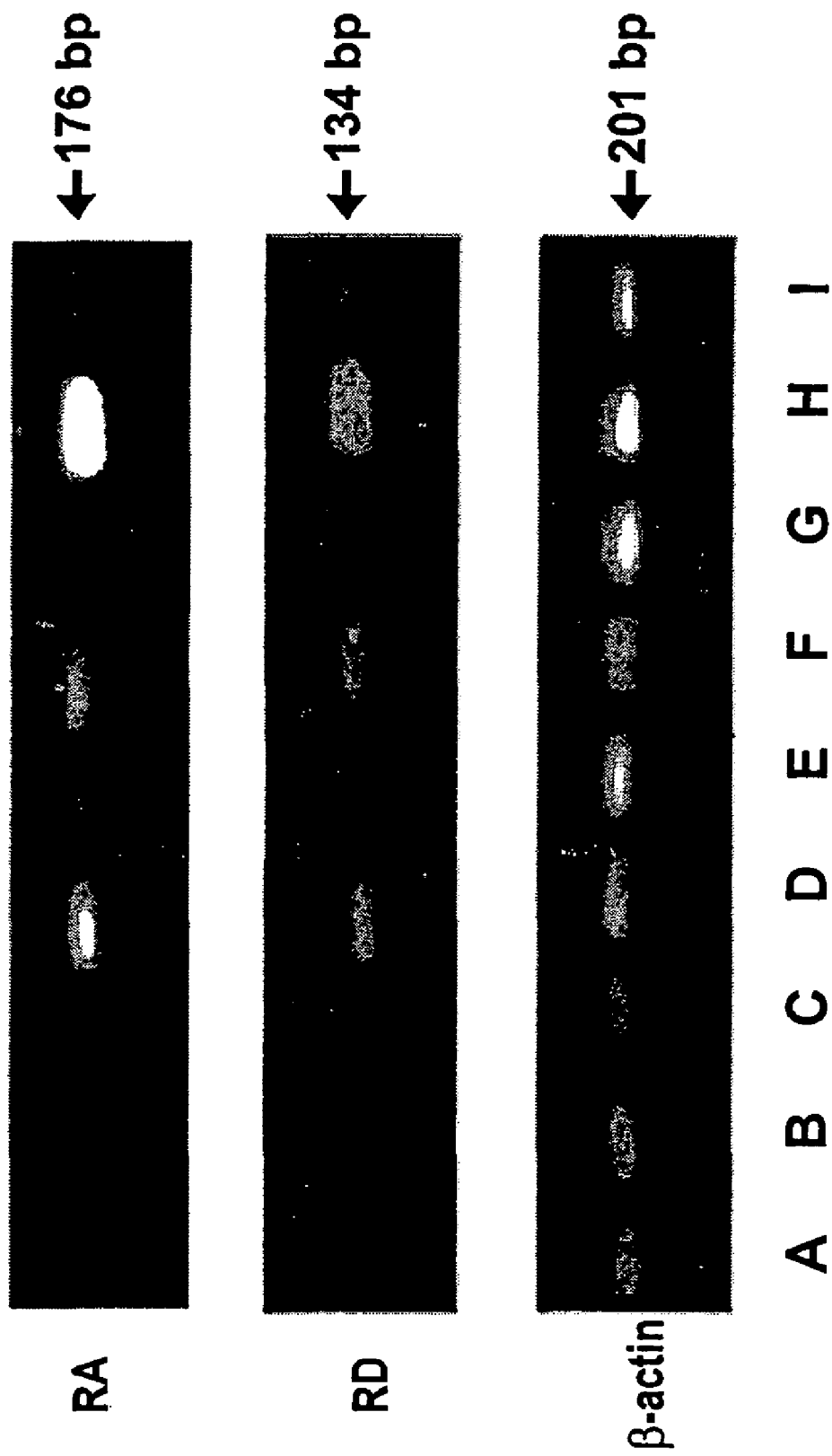
FIG. 4—Rice plasmid DNA detection by PCR in paraffin-embedded SLN after MLM. Representative examples of PCR amplification with RA, RD and β-actin PCR on paraffin-embedded SLN. MLM performed with rice plasmid DNA and blue dye in the footpad. Lane A is the negative control, muscle tissue. Lanes B-F are SLN (popliteal):MLM was performed with 0, 0.625, 1.25, 2.5, or 5 µg of rice plasmid DNA, respectively. Lanes G-I are mesenteric lymph nodes: MLM performed with 0, 0.625 or 5 µg of rice plasmid DNA, respectively.

In human SLND, both frozen and paraffin sections are used to assess for metastases. MLM studies were performed at various dosages of plasmid DNA and assessed in both frozen and paraffin-embedded SLN. The extracted DNA from multiple sections was analyzed by PCR using RA and RD primer sets. In FIG. 4 representative PCR detection of different dosages of plasmid DNA used in MLM is shown. The studies demonstrated that plasmid DNA used in MLM could be detected efficiently in both frozen and paraffin-embedded SLN.

Figure 5:
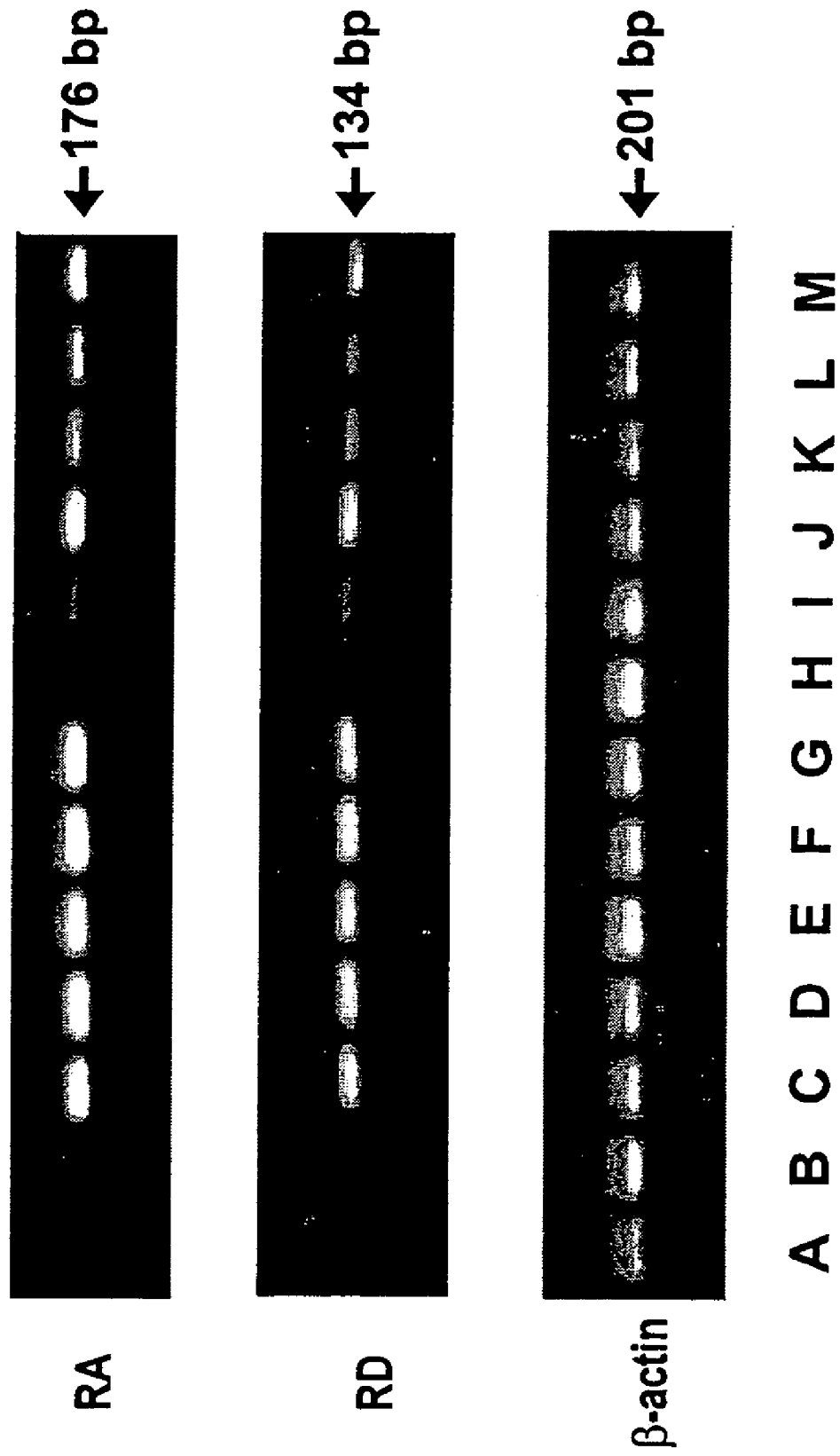
FIG. 5—Detection of rDNA by PCR in frozen SLN after MLM. Representative examples of PCR amplification with RA, RD, and β-actin primers on SLN. MLM performed with rDNA and blue in the rat footpad. Lane A is the negative control, muscle tissue. Lanes B-G are SLN (popliteal):MLM performed with 0, 0.625, 1.25, 2.5, 5 or 10 µg of rDNA, respectively. Lanes H-M are mesenteric lymph nodes:MLM performed with 0, 0.625, 1.25, 2.5, 5, or 10 µg of rDNA, respectively.

MLM with rDNA. To further simplify the MLM procedure, we produced a smaller DNA marker using a linear rice DNA fragment. The advantage of linear DNA (non-vector) is the elimination of potential plasmid promoter element insertion into the host genome. An additional advantage with this approach is the avoidance of pooling at the injection site and inadequate transit to the SLN, which may occur with the larger plasmid DNA. Using rDNA, the same MLM procedures were applied to identify the SLN. First, the rDNA was used in MLM, and the efficiency of SLN targeting was assessed at various dosages ranging from 0.625 to 1.25 µg of rDNA. Frozen SLNs were isolated and assessed by PCR (FIG. 5). The rDNA was detected in SLN when as low as 0.625 µg was used in MLM however, at higher dosages it was more consistent. The detection of rDNA by PCR primers RA and RD was highly efficient at 1.25 µg (Table 2). There was 100% detection of the rDNA using the RD primer set alone in frozen SLN. In all control animals in which blue dye alone was used in MLM the PCR with RA and RD primers were negative. The rDNA was not degraded in frozen SLN kept for over a month at −30° C. as detected by PCR.

Figure 6:
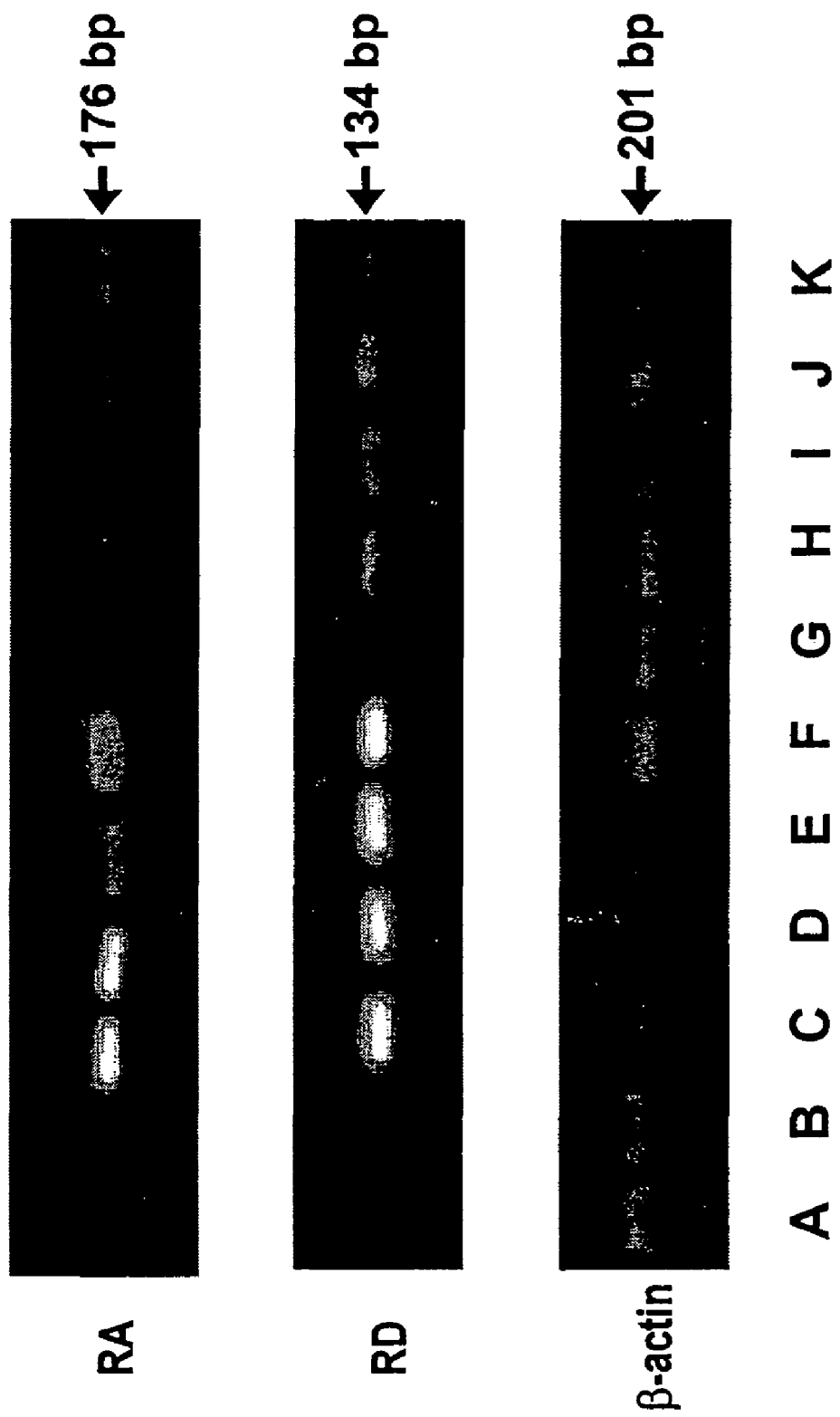
FIG. 6—Detection of rDNA by PCR in paraffin-embedded SLN after MLM. Representative examples of PCR amplification with RA, RD, and β-actin primers on paraffin-embedded SLN. MLM performed with rDNA and blue dye in the rat footpad. Lane A is the negative control, muscle tissue. Lanes B-F are SLN (popliteal):MLM performed with 0, 0.625, 1.25, 2.5, or 5 µg of rDNA, respectively. Lanes G-K are mesenteric SLN:MLM performed with 0, 0.625, 1.25, 2.5, or 5 µg of rDNA, respectively.

We further investigated MLM using rDNA in paraffin-embedded SLN. The PCR assay was performed as described above on excised SLN that were formalin fixed and paraffin-embedded. Initially serial sections of the paraffin-embedded tissue were extracted for DNA and the PCR assay was performed to assess multiple primer sets and conditions. Representative examples of rDNA detection by PCR in SLN when different dosages of rDNA in MLM were used are shown in FIG. 6. In assessment of multiple animals, the rDNA detection in the SLN was highly efficient and could be detected by both RA and RD PCR primers in 100% of the specimens, by evaluating one to three tissue sections, when 1.25 µg of DNA was used for MLM (Table 2). These MLM studies with rDNA indicate that low copies of the DNA marker can be detected from DNA isolated from a few paraffin-embedded sections.

Mesenteric SLN analysis. Clinically, we have successfully performed lymphatic mapping in patients with early stage colorectal cancer to identify SLN(s) that may harbor micrometastasis (8,16). These studies have been very successful in identifying occult metastasis in the SLN from these patients. As a model for MLM of colorectal cancer we developed a protocol targeting the mesenteric lymph nodes in the rat. Representative PCR detection with primer sets RA and RD for plasmid DNA and rDNA in frozen mesenteric SLN is shown in FIGS. 3 and 5, and in paraffin-embedded mesenteric SLN in FIGS. 4 and 6. If blue dye alone was used for lymphatic mapping of the SLN were negative when assessed by PCR with either primer sets RA or RD. The detection of rDNA in frozen mesenteric SLN was 100%, whereas in the paraffin-embedded SLN the detection was 50%.

Figure 7:
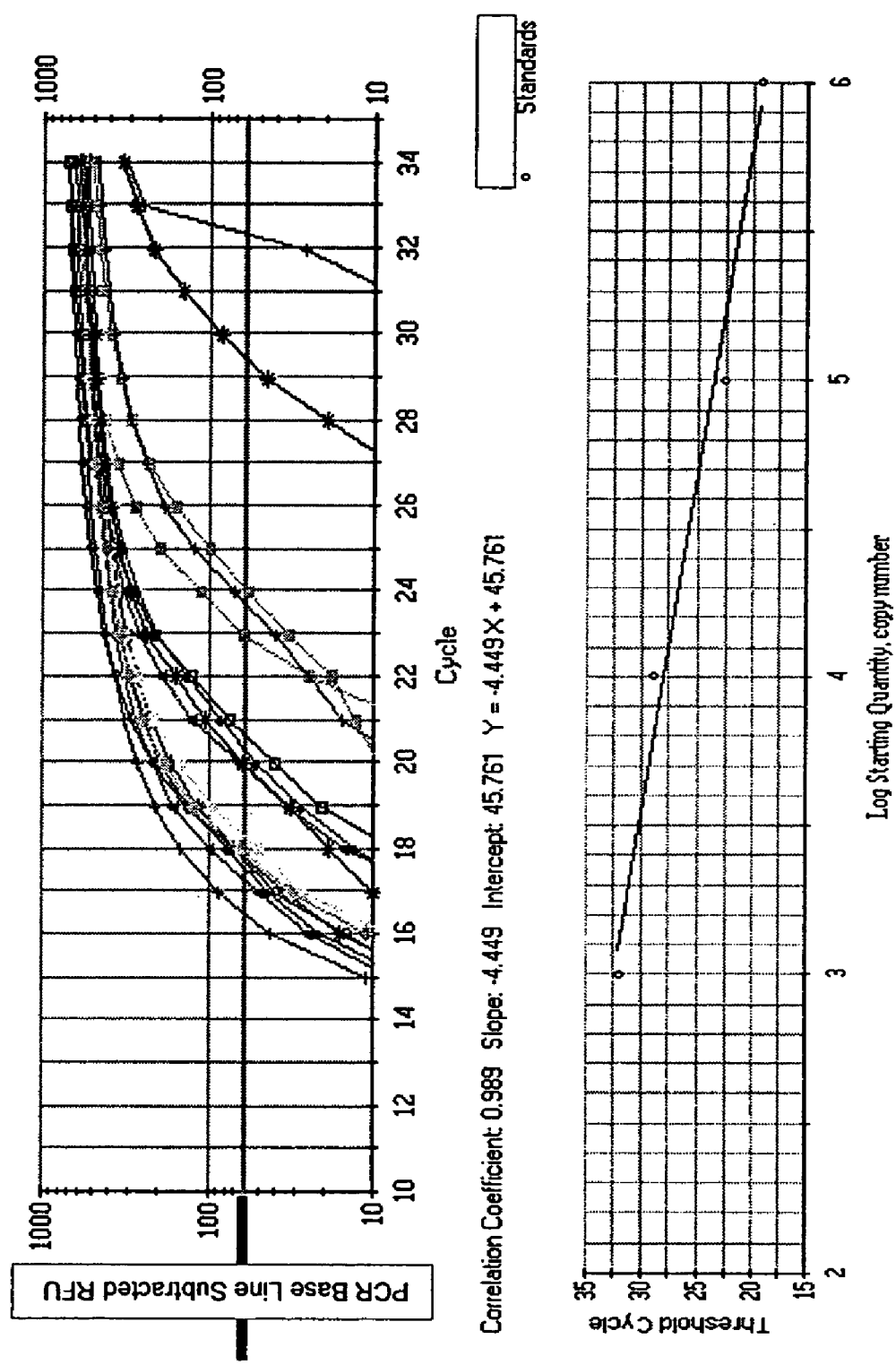
FIG. 7—Representative example of real-time PCR quantitation. Top: Quantitation of rDNA in SLN is shown as log reporter fluorescence units (RFU). Samples of unknown copies of rDNA are amplified and the RFU are determined. Horizontal red line is the threshold cycle. Bottom: Standard curve for determining rDNA copy number using known amounts of rice plasmid DNA in real-time PCR.

Quantitation of gene copies in the SLN. Quantitation of DNA in the SLN after MLM allows us to determine the level of the DNA marker that reached the SLN. To quantify the copies of the DNA marker in the SLN after MLM, we performed quantitative real-time PCR (FIG. 7). Animals were injected in the footpad with two different dosages of rDNA, 2.5 and 1.25 µg. Control animals were those in which LM was performed with the blue dye only. Using 500 ng of DNA in real-time PCR, $5.29 \times 10^6$ copies of rice gene was found in the SLN when MLM was performed with 2.5 µg DNA marker whereas, $2.00 \times 10^6$ copies were found in the SLN when MLM was performed with 1.25 µg of DNA marker (Table 3). Decreasing copy numbers of rDNA were found when lesser amounts of DNA templates were assessed.

Figure 8A:
FIGS. 8A-8C—Representative photographs of in situ staining with biotinylated rDNA in the SLN.
Figure 8B:
Figure 8C:
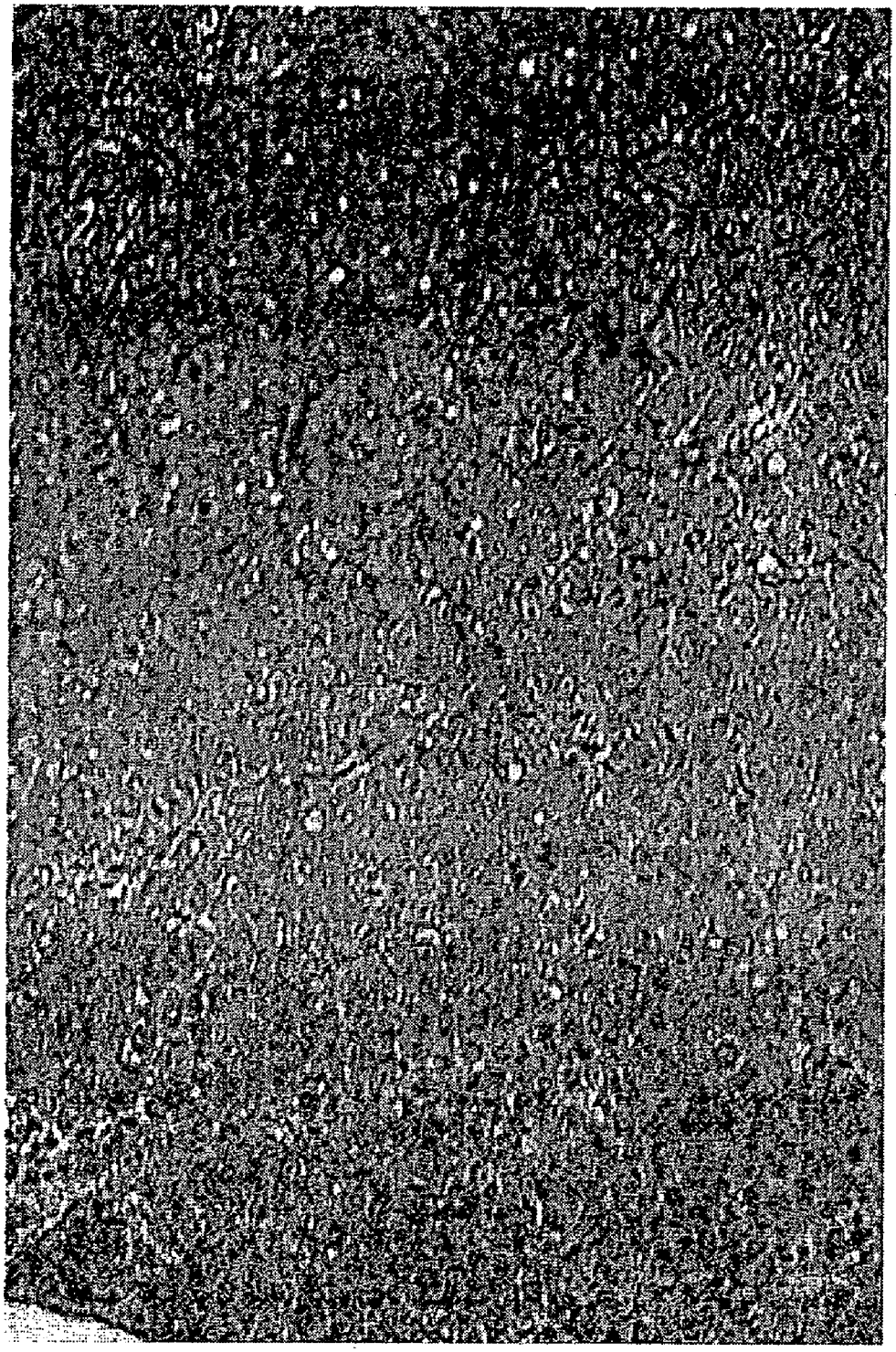

Histochemical verification of the DNA marker. To verify the presence of the DNA marker in the SLN, we performed in situ hybridization. MLM was performing using a 5' prime biotin labeled rDNA mixed with blue dye by injection into the footpad. The SLN was dissected, fixed and paraffin-embedded as previously described. Tissue sections were cut and stained with avidin-conjugated peroxidase, counterstained, and developed for light microscopy assessment. Analysis of all 10-12 sections demonstrated that the majority of the labeled marker was in the subcapsular and paratrabecular sinus of the SLN (FIG. 8). The DNA marker was detected in all of the sections stained demonstrating the utility of using a limited number of sections for DNA analysis. These studies indicate that the marker can be used to direct the viewer to potential sites in the SLN where metastatic tumor cells may distribute. The studies also validate by visual detection the presence of the DNA marker in the SLN after MLM.

Rat tumor metastasis model. There are very few animal models in which tumor progression occurs sequentially from the primary tumor to the draining lymph nodes via the lymphatics and then to systemic sites as in human breast cancer. The mammary rat tumor model MAT13762 progresses in a similar manner as human breast cancer from the primary tumor to the draining lymph node. One million exponentially growing MAT13762 cells were inoculated into the rat footpad (n=12 animals). Within approximately 14 days the tumor was easily identifiable in the footpad. MLM was performed using rDNA in blue dye by injection around the tumor area in a manner similar to human breast cancer SLN mapping. The popliteal SLN was identified, dissected, and processed for DNA or formalin fixed and paraffin-embedded for histopathologic analysis. Serial sections were cut and H&E stained for analysis of tumor metastasis. Histochemical analysis of the SLN indicated micrometastasis presence in the SLN identified by MLM in all animals. PCR analysis of adjacent serial sections from SLN containing tumor cells confirmed by H&E demonstrated the presence of rDNA in all cases.

Figure 9:
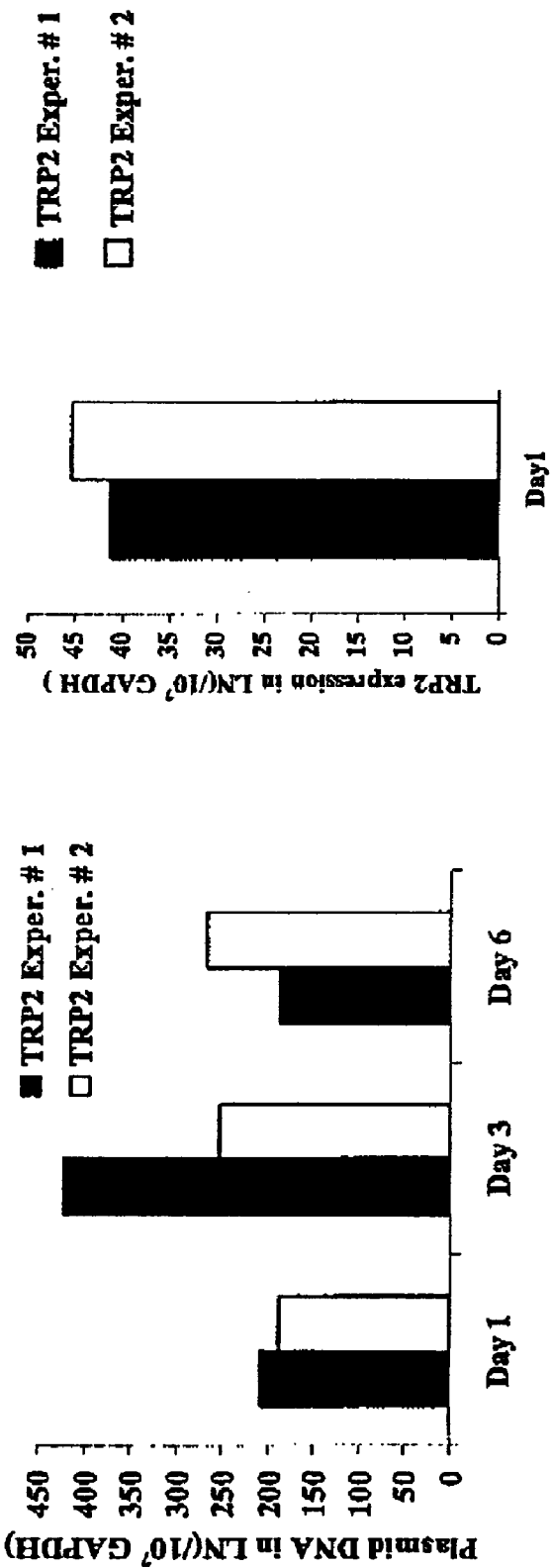
FIG. 9—Molecular Lymphatic Mapping: Gene Expression. Left Panel—Represents two experiments of plasmid DNA containing human TRP-2 (tyrosinase related protein-2) gene. Injection of DNA was in the lymphatics (molecular lymphatic mapping) of the mouse hind leg flank. Inguinal lymph node removed 1 day, 3 days and 6 days later. DNA Real Time PCR specific for TRP-2 was performed to detect plasmid DNA in lymph node. All lymph nodes were positive for plasmid DNA. Right Panel—Represents two experiments of plasmid DNA containing human TRP-2 gene expression. Injection of DNA was as in left panel. Real Time RT-PCR analysis was performed on mRNA isolated from lymph nodes on day 1. In both experiments, human TRP-2 mRNA was detected.

FIG. 9 provides an additional in vivo example, using both plasmid DNA detection and gene expression to map the SLN.

TABLE 1

MLM with rice plasmid DNA: PCR detection in the SLN

| | Frozen popliteal SLN | | | Paraffin-embedded popliteal SLN | | |
|---|---|---|---|---|---|---|
| | RA primer | RD primer | RA or RD primer | RA primer | RD primer | RA or RD primer |
| Detection of rice plasmid | 4/4 (100%) | 4/4 (100%) | 4/4 (100%) | 3/4 (75%) | 3/4 (75%) | 3/4 (75%) |
| Detection of rice plasmid | 5/5 (100%) | 5/5 (100%) | 5/5 (100%) | 4/4 (100%) | 4/4 (100%) | 4/4 (100%) |

MLM was performed with 2.5 μg of rice plasmid DNA. Results shown indicate number of rats in which molecular marker was detected in SLN by PCR after MLM. RA or RD primer results indicate positive PCR for either marker.

TABLE 2

MLM with rDNA: PCR detection in the SLN

| | Frozen popliteal SLN | | | Paraffin-embedded popliteal SLN | | |
|---|---|---|---|---|---|---|
| | RA primer | RD primer | RA or RD primer | RA primer | RD primer | RA or RD primer |
| Detection of rDNA | 11/12 (92%) | 12/12 (100%) | 12/12 (100%) | 26/26 (100%) | 26/26 (100%) | 26/26 (100%) |
| Detection of rDNA | 9/9 (100%) | 9/9 (100%) | 9/9 (100%) | 2/4 (50%) | 2/4 (50%) | 2/4 (50%) |

MLM was performed with 1.25 μg of rDNA. Results shown indicate number of rats in which molecular marker was detected in SLN by PCR after MLM. RA or RD primer results indicate positive PCR for either marker.

TABLE 3

Quantitation of DNA marker copies in SLN after MLM

| DNA (μg) used in MLM | DNA in PCR (ng) | Threshold cycle | DNA copy number in SLN |
|---|---|---|---|
| 2.5 | 500 | 16.3 | 5,290,000 |
| | 100 | 17.6 | 2,720,000 |
| | 10 | 20.5 | 590,000 |
| 1.25 | 500 | 18.2 | 2,000,000 |
| | 100 | 20.2 | 694,000 |
| | 10 | 23.9 | 93,400 |
| 0 | 500 | >35 | 0 |
| | 100 | >35 | 0 |
| | 10 | >35 | 0 |

Representative of individual rat SLN after MLM with 2.5 or 1.25 μg rDNA.
Real-time PCR performed on DNA isolated from SLN after MLM with rDNA.

All of the compositions and methods disclosed and claimed herein can be made and executed without undue experimentation in light of the present disclosure. While the compositions and method of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,162,282
U.S. Pat. No. 4,279,887
U.S. Pat. No. 4,310,505
U.S. Pat. No. 4,533,254
U.S. Pat. No. 4,683,195
U.S. Pat. No. 4,683,202
U.S. Pat. No. 4,728,575
U.S. Pat. No. 4,728,578
U.S. Pat. No. 4,735,210
U.S. Pat. No. 4,737,323
U.S. Pat. No. 4,782,840
U.S. Pat. No. 4,797,368
U.S. Pat. No. 4,800,159
U.S. Pat. No. 4,801,803
U.S. Pat. No. 4,883,750
U.S. Pat. No. 4,889,991
U.S. Pat. No. 4,921,706
U.S. Pat. No. 4,946,778
U.S. Pat. No. 5,008,546
U.S. Pat. No. 5,070,878
U.S. Pat. No. 5,111,828
U.S. Pat. No. 5,139,941
U.S. Pat. No. 5,154,913
U.S. Pat. No. 5,279,721
U.S. Pat. No. 5,383,456
U.S. Pat. No. 5,580,859
U.S. Pat. No. 5,589,466

U.S. Pat. No. 5,656,610
U.S. Pat. No. 5,702,932
U.S. Pat. No. 5,728,369
U.S. Pat. No. 5,736,524
U.S. Pat. No. 5,776,093
U.S. Pat. No. 5,776,094
U.S. Pat. No. 5,776,095
U.S. Pat. No. 5,780,448
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,879,703
U.S. Pat. No. 5,900,481
U.S. Pat. No. 5,905,024
U.S. Pat. No. 5,910,407
U.S. Pat. No. 5,911,970
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,565
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,136
U.S. Pat. No. 5,994,136
U.S. Pat. No. 5,994,624
U.S. Pat. No. 6,013,516
GB Appl. 2 202 328
GB Appl. 2 193 095
PCT Appl. PCT/US87/00880
PCT Appl. PCT/US88/10315
PCT Appl. PCT/US89/01025
PCT Appl. PCT/US85/01161
PCT Appl. PCT/US89/05040
PCT Appl. WO 99/18933
European Appl. 320 308
European Appl. 329 822
European Appl. 0273085
Fr. Patent Pub. 2,642,972
Almendro et al., *J. Immunol.*, 157(12): 5411-5421, 1996.
Arap et al., *Cancer Res.*, 55(6): 1351-1354, 1995.
Ausubel et al., In: *Current Protocols in Molecular Biology*, John, Wiley and Sons, Inc, New York, 1994.
Baichwal and Sugden, In: *Gene Transfer*, Kucherlapati (ed.), New York, Plenum Press, 117-148, 1986.
Bakhshi, et al., *Cell*, 41(3): 899-906, 1985.
Bangham, et al., *J. Mol. Biol.*, 13: 238-252, 1965.
Bellus, *J. Macromol. Sci. Pure Appl. Chem*, A31(1): 1355-1376, 1994.
Bilchik et al., *J. Cancer*, 4: 351-358, 1998.
Bilchik et al., *J. Clin. Oncol.*, 19: 1128-1136, 2001.
Blasdel and Salama, *Nature*, 321: 579, 1986.
Blomer et al., *J. Virol.*, 71(9): 6641-6649, 1997.
Bodine and Ley, *EMBO J.*, 6: 2997, 1987.
Boshart et al., *Cell*, 41: 521, 1985.
Bostick et al., *Arch. Surg.*, 134: 43-49, 1999a.
Bostick et al., *Int. J. Cancer*, 79: 645-651, 1998a.
Bostick et al., *J. Clin. Oncol.*, 17: 3238-3244, 1999b.
Bostick et al., *N. Engl. J. Med.*, 339: 1643-1644, 1998b.
Brobeil et al., *Surg. Oncol. Clinics North Amer.*, 8: 435-445, 1999.
Caldas et al., *Nat. Genet.*, 8(1): 27-32, 1994.
Canfield et al., *Methods Enzymol.*, 189: 418-422, 1990.
Carbonelli et al., *FEMS Microbiol. Lett.*, 177(1): 75-82, 1999.
Chandler et al., *Proc. Nat'l Acad. Sci. USA*, 94(8): 3596-601, 1997.
Cheng et al., *Cancer Res.*, 54(21): 5547-5551, 1994.
Cleary and Sklar, *Proc. Nat'l Acad. Sci. USA*, (21): 7439-7443, 1985.
Cleary et al., *J. Exp. Med.*, 164(1): 315-320, 1986.
Cocea, *Biotechniques*, 23(5): 814-816, 1997.
Cochran et al., *Cancer*, 89: 236-241, 2000.
Cotten et al., *Proc. Nat'l Acad. Sci. USA*, 89(13): 6094-6098, 1992.
Coupar et al., *Gene*, 68: 1-10, 1988.
Cox et al., *Ann. Surg.*, 227: 645-651, 1998.
Curiel, *Nat. Immun.*, 13(2-3): 141-64, 1994.
Deamer and Uster, In: *Liposomes*, Ostro (ed), Marcel Dekker, Inc., NY, 27-52, 1983.
DeVita et al., In: *Cancer, principles and practice of oncology*, 1(4): 40, Harris et al. (eds.) Lippincott Co., Philadelphia, Pa., 1993.
Disbray & Rack, In: *Histologic Laboratory Methods*, Livingstone (London), 1970.
El-Gorab, *Biochim. Biophys. Acta*, 306(1): 58-66, 1973.
Fraley et al., *Proc. Nat'l Acad. Sci. USA*, 76: 3348-3352, 1979.
Friedmann, *Science*, 244: 1275-1281, 1989.
Frohman, In: *PCR Protocols: A guide to methods and applications*, Academic Press, NY, 1990.
Gabizon et al., *Cancer Res.*, 50(19): 6371-6378, 1996.

Ghosh and Bachhawat, In: *Liver diseases, targeted diagnosis and therapy using specific receptors and ligands*, Wu and Wu (eds.), NY, Marel Dekker, 87-104, 1991.
Giuliano et al., *Ann. Surg.*, 222: 394-399, 1995.
Giuliano et al., *Ann. Surg.*, 220(3): 391-401, 1994.
Giuliano et al., *J. Clin. Oncol.*, 15: 2345-2350, 1997.
Giuliano et al., *J. Clin. Oncol.*, 18: 2553-2559, 2000.
Gregoriadis and Davis, *Biochem. Biophys. Res. Commun.*, 89(4): 1287-1293, 1979.
Grinvald et al., *Physiological Reviews*, 68: 1285, 1988.
Grunhaus et al., *Seminar in Virology*, 200(2): 535-546, 1992.
Haigh and Giuliano, In: *Cancer: principles and practice of oncology*, Devita et al. (eds.), Lippincott-Raven, 14: 1-11, 2000.
Haigh et al., *Cancer*, 92: 535-441, 2001.
Harlow et al., *Semin. Surg. Oncol.*, 20: 224-229, 2001.
Hill et al., *Ann. Surg.*, 229: 528-535, 1999.
Hollstein et al., *Science*, 253(5015): 49-53, 1991.
Hoon et al., *Cancer Res.*, 44: 2406-2409, 1984.
Hoon et al., *Int. J. Cancer*, 69: 369-374, 1996.
Horwich et al., *J. Virology.*, 64: 642-650, 1990.
Hussussian et al., *Nat. Genet.*, 8(1): 15-21, 1994.
Innis et al., *Proc. Nat'l Acad. Sci. USA*, 85(24): 9436-9440, 1988.
John et al., *J. Med. Chem.*, 37: 1737-1739, 1994
Kamb et al., *Nat. Genet.*, 8(1): 23-2, 1994.
Kaneda and Hoon, In: *Drugs*, UK, PharmaPress Ltd, 301-311, 2001.
Kaneda et al., *Science*, 243: 375-378, 1989.
Kato et al, *J. Biol. Chem.*, 266: 3361-3364, 1991.
Kauer, *Nature*, 331: 166, 1988.
Kelemen et al., *Arch. Surg.*, 133: 288-292, 1998.
Kelleher and Vos, *Biotechniques*, 17(6): 1110-7, 1994.
Kerr et al., *Br. J. Cancer*, 26(4): 239-257, 1972.
Kitagawa et al., *Surg. Oncol. Clinics North Amer.*, 80: 1799-1809, 2000.
Kraus et al. *FEBS Lett.*, 428(3): 165-170, 1998.
Kwoh et al., *Proc. Nat'l Acad. Sci. USA*, 86: 1173, 1989.
Lareyre et al., *J. Biol. Chem.*, 274(12): 8282-8290, 1999.
Laughlin et al., *J. Virology*, 60(2): 515-524, 1986.
Lebkowski et al., *Mol. Cell. Biol.*, 8(10): 3988-3996, 1988.
Lee et al., *J. Auton. Nerv. Syst.* 74(2-3): 86-90, 1997.
Levenson et al., *Hum. Gene Ther.*, 20; 9(8): 1233-1236, 1998.
Lieke et al., *Annu. Rev. Physiol.*, 51: 543, 1989.
Liptay et al., *J. Clin. Oncol.*, 20(8): 1984, 2002.
Macejak and Sarnow, *Nature*, 353: 90-94, 1991.
Maniatis, et al., In: *Molecular Cloning*, A Laboratory Manual, Cold Spring Harbor Press, Cold Spring Harbor, N.Y., 1988.
Mann et al., *Cell*, 33: 153-159, 1983.
Mayer et al., *Biochim. Biophys. Acta*, 858(1): 161-168, 1986.
Mayhew et al., *Biochim. Biophys. Acta*, 775(2): 169-174, 1984.
McLaughlin et al., *J. Virology*, 62(6): 1963-1973, 1988.
Meyniel et al., *Acad. Sci. Paris*, 311: 13-18, 1990.
Michelot et al., *J. Nucl. Med.*, 32: 1573-1580, 1991.
Miller et al., *Am. J. Clin. Oncol.*, 15(3): 216-221, 1992.
Mori et al., *Insectes Sociaux*, 47: 7-10, 2000.
Morton et al., *Ann. Surg.*, 230: 453-463, 1999.
Morton et al., *Arch. Surg.*, 127: 392-399, 1992.
Murphy et al., *J. Med. Chem.*, 33: 171-178, 1990.
Muzyczka, *Curr. Top Microbiol. Immunol.*, 158: 97-129, 1992.
Nabel and Baltimore, *Nature*, 326: 711-713, 1987.
Naldini et al., *Science*, 272(5259): 263-267, 1996.
Nicolas and Rubenstein, In: *Vectors: A survey of molecular cloning vectors and their uses*, Rodriguez and Denhardt (eds.), Stoneham: Butterworth, 493-513, 1988.
Nicolau and Sene, *Biochim. Biophys. Acta*, 721: 185-190, 1982.
Nicolau et al., *Methods Enzymol.*, 149: 157-176, 1987.
Nieroda et al., *Surg. Gynecol. Obstet.*, 169(1): 35-40, 1989.
Nobori et al., *Nature*, 368(6473): 753-756, 1994.
Nomoto et al., *Gene*, 236(2): 259-271, 1999.
Ohara et al., *Proc. Nat'l Acad. Sci. USA*, 86: 5673-5677, 1989.
Okamoto et al., *Gene Ther.*, 4: 969-976, 1997.
Okamoto et al., *Proc. Nat'l Acad. Sci. USA*, 1(23): 11045-11049, 1994.
Orlow et al., *Cancer Res.*, 54(11): 2848-2851, 1994.
Paskind et al., *J Virology*, 67: 242-248, 1975.
Pelletier and Sonenberg, *Nature*, 334: 320-325, 1988.
Ridgeway, In: *Vectors: A survey of molecular cloning vectors and their uses*, Stoneham: Butterworth, 467-492, 1988.
Roux et al., *Proc. Nat'l Acad. Sci. USA*, 86: 9079-9083, 1989.
Saha et al., *Ann. Surg. Oncol.*, 7: 120-124, 2000.
Sambrook et al., In: *Molecular cloning*, Cold Spring Harbor Laboratory Press, Cold Spring Harbor, N.Y., 1989.
Serrano et al., *Nature*, 366: 704-707, 1993.
Serrano et al., *Science*, 267(5195): 249-252, 1995.
Shoaib et al., *Head Neck*, 22(7): 733, 2000.
Sugarbaker, *Cancer Biol. Rev.*, 2: 235, 1981.
Szoka and Papahadjopoulos, *Proc. Nat'l Acad. Sci.*, 75: 4194-4198, 1978.
Temin, In: *Gene Transfer*, Kucherlapati (ed.), NY, Plenum Press, 149-188, 1986.
Templeton et al., *Nat. Biotechnol.*, 15(7): 647-652, 1997.
Tratschin et al., *Mol. Cell. Biol.*, 4: 2072-2081, 1984.
Tsioulias et al., *Arch. Surg.*, 135: 926-932, 2000.
Tsujimoto and Croce, *Proc. Nat'l Acad. Sci. USA*, 83(14): 5214-5218, 1986.
Tsujimoto et al., *Science*, 228(4706): 1440-1443, 1985.
Tsumaki et al., *J. Biol. Chem.*, 273(36): 22861-22864, 1998.
Turner et al., *Ann. Surg.*, 226: 271-276, 1997.
Uren et. al, *J. Nucl. Med.*, 34: 1435-1440, 1993.
Veronesi et al., *Lancet*, 349: 1864-1867, 1997.
Villner et al. In: *Multiple sigma and PCP receptor ligands: mechanisms for neuromodulation and neuroprotection*, Kamenka et al., (eds.) NPP Books, 341-353, 1992.
Walker et al., *Pharmacol. Reviews*, 42: 355-400, 1990.
Walker et al., *Proc. Nat'l Acad. Sci. USA*, 89: 392-396 1992.
Wascher et al., *Br. J. Cancer*, 85(9): 1340-6, 2001.
Wawroschek et al., *J. Urol.*, 166(5): 1715, 2001.
Weinberg, *Science*, 254(5035): 1138-1146, 1991.
Whitcombe et al., *Nature Biotechnology*, 17: 804-807, 2000.
Wilson et al., *Science*, 244: 1344-1346, 1989.
Wong et al., *Gene*, 10: 87-94, 1980.
Wu and Wu, *Biochemistry*, 27: 887-892, 1988.
Wu and Wu, *J. Biol. Chem.*, 262: 4429-4432, 1987.
Wu et al., *Biochem. Biophys. Res. Commun.*, 233(1): 221-6, 1997.
Zhao-Emonet et al., *Biochem. Biophys. Acta*, 1442(2-3): 109-19, 1998.
Zufferey et al., *Nat. Biotechnol.*, 15(9): 871-875, 1997.

What is claimed is:

1. A method for identifying sentinel lymph nodes comprising:
   (a) administering a composition comprising a marker nucleic acid segment to a human subject regional to a sentinel lymph node; and
   (b) determining the presence or absence of the marker nucleic acid segment in a lymph node;

wherein the presence of said marker nucleic acid segment in the lymph node identifies the lymph node as a sentinel lymph node.

2. The method of claim 1, wherein the marker nucleic acid segment is a prokaryotic nucleic acid segment.

3. The method of claim 2, wherein the prokaryotic nucleic acid segment is bacterial or viral nucleic acid segment.

4. The method of claim 1, wherein the marker nucleic acid segment is a eukaryotic nucleic acid segment.

5. The method of claim 4, wherein the eukaryotic nucleic acid segment is a plant nucleic acid segment.

6. The method of claim 5, wherein the plant nucleic acid segment is a rice nucleic acid segment.

7. The method of claim 1, wherein the human subject is at risk of cancer.

8. The method of claim 7, wherein the human subject is at risk of cancer metastasis.

9. The method of claim 1, wherein the human subject has been diagnosed with a solid cancer.

10. The method of claim 1, wherein the human subject previously has been diagnosed with cancer and is believed to be in remission.

11. The method of claim 7, wherein the cancer is solid tumor cancer selected from the group consisting of breast cancer, gastrointestinal cancer, melanoma, lymphoma, squamous carcinoma, merkel cell cancer, colorectal cancer, pancreatic cancer, gastric cancer, thyroid cancer, renal cancer, bladder cancer, prostate cancer, esophageal cancer, vulvar cancer, ovarian cancer, penile cancer, head & neck cancer and lung cancer.

12. The method of claim 9, wherein the marker nucleic acid is administered by injection into the lymphatic system proximal to the solid tumor.

13. The method of claim 1, wherein the marker nucleic acid segment comprises a linear, double-stranded DNA molecule.

14. The method of claim 1, wherein the composition further comprises a dye.

15. The method of claim 14, wherein the dye is selected from the group consisting of isosulfan blue, direct sky blue, pentamine, guajazulen blue, or methylene blue.

16. The method of claim 1, wherein the composition further comprises a radioactive isotope.

17. The method of claim 16, wherein the radioactive isotope is technetium$^{99}$.

18. The method of claim 1, further comprising the step of removing a lymph node from said subject, wherein the removal occurs after step (a) and before step (b).

19. The method of claim 18, wherein the removed lymph node is frozen.

20. The method of claim 18, wherein the removed lymph node is embedded in preserving material.

21. The method of claim 20, wherein the removed lymph node is embedded in paraffin.

22. The method of claim 19, further comprising performing histopathology upon the removed lymph node.

23. The method of claim 22, wherein histophathology comprises hematoxylin staining.

24. The method of claim 23, wherein histophathology further comprises eosin staining.

25. The method of claim 22, wherein histophathology comprises immunohistochemistry.

26. The method of claim 22, wherein histophathology comprises in situ hybridization.

27. The method of claim 1, wherein identifying comprises nucleic acid hybridization to said marker nucleic acid segment.

28. The method of claim 27, further comprising nucleic acid amplification of said marker nucleic acid segment.

29. The method of claim 28, wherein nucleic acid amplification comprises PCR.

30. The method of claim 29, wherein PCR comprises quantitative PCR.

31. The method of claim 27, wherein the nucleic acid hybridization comprises hybridization of a labeled probe to nucleic acids isolated from cells of the removed lymph node.

32. The method of claim 31, wherein the probe is labeled with a fluorophore.

33. The method of claim 31, wherein the probe is labeled with a radioactive isotope.

34. The method of claim 31, wherein the probe is labeled with a ligand.

35. The method of claim 34, wherein the ligand is biotin.

36. The method of claim 7, further comprising providing to the human subject chemotherapy, radiotherapy, hormonal therapy or immunotherapy.

37. The method of claim 7, further comprising surgical removal of primary tumor tissue.

38. The method of claim 18, wherein the removed lymph node is a sentinel lymph node.

39. The method of claim 18, further comprising surgical removal of multiple lymph nodes.

40. The method of claim 38, further comprising assessing the presence or absence of metastatic cells in the sentinel lymph node.

41. The method of claim 40, further comprising making a treatment decision based upon the presence or absence of metastatic cells in the sentinel lymph node.

42. The method of claim 40, further comprising staging the cancer based upon the presence or absence of metastatic cells in the sentinel lymph node.

43. The method of claim 39, further comprising assessing the presence or absence of metastatic cells in an adjacent draining lymph node.

44. The method of claim 43, further comprising making a treatment decision based upon the presence or absence of metastatic cells in the adjacent draining lymph node.

45. The method of claim 43, further comprising staging the cancer based upon the presence or absence of metastatic cells in the adjacent draining lymph node.

46. The method of claim 40, further comprising removing a non-sentinel lymph node based upon the presence of metastatic cells in the removed sentinel lymph node.

47. The method of claim 17, further comprising archival storage of the removed lymph node.

48. The method of claim 40, wherein assessing comprises immunohistochemistry.

49. The method of claim 40, wherein assessing comprises nucleic acid hybridization.

50. The method of claim 49, wherein nucleic acid hybridization further comprises PCR.

51. The method of claim 50, wherein PCR comprises amplification of (a) the marker nucleic acid segment and (b) a nucleic acid tumor marker.

52. The method of claim 51, wherein the marker nucleic acid segment is labeled with a detectable marker.

* * * * *